US008058396B2

(12) United States Patent
Schiemann

(10) Patent No.: US 8,058,396 B2
(45) Date of Patent: Nov. 15, 2011

(54) CYSTATIN C AS AN ANTAGONIST OF TGF-β AND METHODS RELATED THERETO

(75) Inventor: William P. Schiemann, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 12/782,014

(22) Filed: May 18, 2010

(65) Prior Publication Data

US 2010/0267644 A1    Oct. 21, 2010

Related U.S. Application Data

(63) Continuation of application No. 11/852,909, filed on Sep. 10, 2007, now Pat. No. 7,749,958, which is a continuation of application No. 10/967,093, filed on Oct. 15, 2004, now Pat. No. 7,282,477.

(60) Provisional application No. 60/511,794, filed on Oct. 15, 2003.

(51) Int. Cl.
*C07K 530/35* (2006.01)
*C07K 14/00* (2006.01)

(52) U.S. Cl. ........................ 530/350; 530/402

(58) Field of Classification Search .......... None
See application file for complete search history.

(56) References Cited

U.S. PATENT DOCUMENTS

| 5,935,817 | A |   | 8/1999  | Bandman et al. |           |
|-----------|---|---|---------|----------------|-----------|
| 6,534,477 | B2|   | 3/2003  | Nakai et al.   |           |
| 7,282,477 | B2|   | 10/2007 | Schiemann      |           |
| 7,749,958 | B2|   | 7/2010  | Schiemann      |           |
| 2002/0086019 | A1 | | 7/2002 | Wolf et al.    |           |
| 2002/0102711 | A1 | | 8/2002 | Bandman et al. |           |
| 2005/0255114 | A1 | * | 11/2005 | Labat et al.  | 424/146.1 |

FOREIGN PATENT DOCUMENTS

DE   3724581   2/1989

OTHER PUBLICATIONS

Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Esnard et al. 1988. FEBS 236:475-478.*
Barrett et al., "The place of human gamma-trace (cystatin C) amongst the cysteine proteinase inhibitors," Biochem Biophys Res Commun. Apr. 30, 1984;120(2):631-6.
Branton et al., "TGF-β and fibrosis," Microbes and Infection, vol. 1, 1999, pp. 1349-1365.
Brown et al., "Friends and relations of the cystatin superfamily—new members and their evolution," Protein Sci. Jan. 1997;6(1):5-12.
Clark et al., "Transforming growth factor-beta (TGF-β)," Int. J. of Biochem. and Cell Biol.,vol. 30, 1998, pp. 293-298.
Cornwall et al., "At the Cutting Edge: A new subgroup of the family 2 cystatins," Mol. And Cell. Endocr., vol. 200, 2003, pp. 1-8.

Corticchiato et al., "Cystatin C and Cathepsin B in Human Colon Carcinoma: Expression by Cell Lines and Matrix Degradation," Int. J. of Cancer, vol. 52, 1992, pp. 645-652.
Coulibaly et al., "Modulation of Invasive Properties of Murine Squamous Carcinoma Cells by Heterologous Expression of Cathepsin B and Cystatin C," Int. J. Cancer, vol. 83, 1999, pp. 526-531.
Database Biosis [Online] Biosciences Information Service, Philadelphia, PA, US; 1995, Olafsson I: "The human cystatin C gene promoter: Functional analysis and identification of heterogeneous mRNA" XP002454535 Database accession No. PREV199698607721 & Scandinavian Journal of Clinical and Laboratory Investigation, vol. 55, No. 7, 1995, pp. 597-607, ISSN: 0036-5513.
Database Biosis [Online] Biosciences Information Service, Philadelphia, PA, US; (Jan. 2003), Ogawa Masahiro et al: "In vitro anticancer activities in Caco-2 and HCT-116 cells of recombinant cystatin C prepared by a Pichia expression system." XP002454534 Database accession No. PREV200400128763.
Database Medline [Online] US National Library of Medicine (NLM), Bethesda, MD, US; 1991, Abrahamson M et al: "Regulation of cystatin C activity by serine proteinases." XP002454536 Database accession No. NLM1801727 & Biomedica Biochimica Acta 1991, vol. 50, No. 4-6, 1991, pp. 587-593, ISSN: 0232-766X.
Esnard, et al., "Purification of the Cystatin C-Like Inhibitors From Urine of Nephropathic Rats" Biological Chemistry Hoppe-Seyler, Walter De Gruyter, Berlin, DE, vol. 369, No. Suppl, (May 1988), pp. 219-222, XP001079633 ISSN: 0177-3593.
Gantt, K. et al., "Activation of TGF-beta by *Leishmania chagasi*: importance for parasite survival in macrophages." Journal of Immunology (Baltimore, MD.: 1950), vol. 170, No. 5, Mar. 1, 2003, pp. 2613-2620, XP002454484 ISSN: 0022-1767.
Grubb et al., "Human gamma-trace, a basic microprotein: amino acid sequence and presence in the adenohypophysis ," Proc Natl Acad Sci U S A. May 1982;79(9):3024-7.
Guo et al., "Phorbal Ester Activation of a Proteolytic Cascade Capable of Activating Latent Transforming Growth Factor-β," J. Bioi Chem., vol. 277, 2002, pp. 14829-14837. Konduri et al., "Modulation of cystatin C expression impairs the invasive and tumorigenic potential of human glioblastoma cells," Oncogene. Dec. 12, 2002;21(57):8705-12.
Kos et al., "Cysteine proteinases and their inhibitors in extracellular fluids: markers for diagnosis and prognosis in cancer," Int J Biol Markers. Jan.-Mar. 2000;15(1):84-9.
Massague et al., TGFβ Signaling in Growth Control, Cancer, and Heritable Disorders, Cell, vol. 103, 2000, pp. 295-309.
Ngo et al., "Computational Complexity, Protein Structure Prediction, and the Levinthal Paradox," The Protein Folding Problem and Tertiary Structure Prediction, 1994, pp. 492-495.
Nycander, M. et al., "Two-step mechanism of inhibition of cathepsin B by cystatin C due to displacement of the proteinase occluding loop" FEBS Letters, Elsevier, Amsterdam, NL, vol. 422, No. 1, (Jan. 23, 1998), pp. 61-64, XP004261774 ISSN: 0014-5793.
Ogawa et al., "Enhancement of proteinase inhibitory activity of recombinant human cystatin C using random-centroid optimization," BBA, vol. 1599, 2002, pp. 115-124.

(Continued)

*Primary Examiner* — Shulamith H Shafer
(74) *Attorney, Agent, or Firm* — Sheridan Ross P.C.

(57) ABSTRACT

Disclosed are Cystatin C (CysC) homologues, including CystC homologues that act as antagonists or inhibitors of transforming growth factor-β (TGF-β). Also disclosed are methods to identify CystC homologues that are antagonists or inhibitors of TGF-β and compositions and therapeutic methods using CystC and homologues thereof to regulate the activity of TGF-β, and TGF-β-mediated tumor malignancy and invasion and other TGF-β-mediated fibrotic or proliferative conditions and diseases.

10 Claims, 7 Drawing Sheets

OTHER PUBLICATIONS

Ogawa et al., "In Vitro Anti-Cancer Activities in Caco-2 and HCT-116 Cells of Recombinant Cystatin C Prepared by a Pichia Expression System," J. Med. Food, vol. 6, 2003, pp. 317-322.

Prud'homme, G.J., "Pathobiology of transforming growth factor β in cancer, fibrosis and immunologic disease, and therapeutic considerations," Lab. Invest., vol. 87, 2007, pp. 1077-1091.

Reed, CH., "Diagnostic applications of cystatin C," Br. J. Biomed. Sci., vol. 57, 2000, pp. 323-329.

Sokol, J. P. et al., "The use of cystatin C to inhibit epithelial-mesenchymal transition and morphological transformation stimulated by transforming growth factor-beta," Breast Cancer Research, BCR 2005, vol. 7(5), 2005, pp. R844-R853, XP021011887 ISSN: 1465-542X.

Solem et al., "Transforming growth factor beta regulates cystatin C in serum-free mouse embryo (SFME) cells," Biochem Biophys Res Commun. Oct. 30, 1990;172(2):945-51.

Somanna et al., "Functional Analysis of Cathepsin B-like Cysteine Proteases from *Leishmania donovani* Complex," J. Biol. Chem., vol. 277(28), 2002, pp. 25305-25312.

Tang et al., "TGF-beta switches from tumor suppressor to prometastatic factor in a model of breast cancer progression.," J Clin Invest. Oct. 2003;112(7):1116-24.

Vray et al., "Review: Immunomodulatory properties of cystatins," Cell Mol Life Sci. 59(9), 2002, pp. 1503-1512.

Wakefield, L. M. et al., "TGF-beta signaling in mammary gland development and tumorigenesis," J Mammary Gland Biol Neoplasia. Jan. 2001;6(1):67-82, XP002454486 ISSN: 1083-3021.

Wei et al. "Cystatin C: Icelandic-like Mutation in an animal model of cerebrovascular beta-amyloidosis", Stroke, Nov. 1996, 27(11), pp. 2080-2085.

Wells, J. A., "Additivity of Mutational Effects in Proteins," Biochemistry, vol. 29(37), Sep. 18, 1990, pp. 8509-8517.

Yan et al., "Molecular Regulation of Human Cathepsin B: Implication in Pathologies," Biol. Chem., vol. 384, Jun. 2003, pp. 845-854.

International Search Report for International (PCT) Patent Application No. PCT/US2004/034181, mailed Mar. 22, 2007.

Written Opinion for International (PCT) Patent Application No. PCT/US2004/034181, mailed Mar. 22, 2007.

International Preliminary Report on Patentability for International (PCT) Patent Application No. PCT/US2004/034181, mailed Apr. 19, 2007.

Supplementary European Search Report for European Patent Application No. 04795359.1, mailed May 27, 2008.

* cited by examiner

CYSTATIN C AS AN ANTAGONIST OF TGF-β AND METHODS RELATED THERETO

CROSS-REFERENCE TO RELATED APPLICATIONS

This application is a continuation of U.S. patent application Ser. No. 11/852,909, filed Sep. 10, 2007, now U.S. Pat. No. 7,749,958, which is a continuation of U.S. patent application Ser. No. 10/967,093, filed Oct. 15, 2004, now U.S. Pat. No. 7,282,477, which claims the benefit of priority under 35 U.S.C. §119(e) from U.S. Provisional Patent Application No. 60/511,794, filed Oct. 15, 2003. The entire disclosure of each application and patent is hereby incorporated by reference for all purposes.

GOVERNMENT RIGHTS

This invention was supported, in part, using funds provided by NIH Grant No. CA095519, awarded by the National Institutes of Health. The government has certain rights to this invention.

REFERENCE TO SEQUENCE LISTING

This application contains a Sequence Listing submitted as an electronic text file named "2879-104-1_ST25.txt", having a size in bytes of 20 kb, and created on 10 Sep. 2007. The information contained in this electronic file is hereby incorporated by reference in its entirety pursuant to 37 CFR §1.52(e)(5).

FIELD OF THE INVENTION

The present invention generally relates to the use of Cystatin C (CysC) as a regulator of transforming growth factor-β (TGF-β), including as a TGF-β antagonist, and to therapeutic methods associated therewith.

BACKGROUND OF THE INVENTION

The cystatin superfamily of cysteine proteinase inhibitors is comprised of three major families: Type 1 cystatins, which are cytosolic and include stefins A and B; Type 2 cystatins, which are present in most bodily fluids and include cystatins C, D, E, F, and S; and Type 3 cystatins, which are present in plasma and include the kininogens and fetuin (1, 2). Collectively, these molecules inactivate cysteine proteinases and thus regulate (i) bone resorption, neutrophil chemotaxis, and tissue inflammation, (ii) hormone processing and antigen presentation, and (ii) resistance to bacterial and viral infections (1-3). Cystatin C (CystC) is a ubiquitously expressed, small molecular weight (~16 kDa) secretory protein that preferentially inactivates cathepsin B, a cysteine proteinase implicated in stimulating cancer cell invasion and metastasis (4, 5), and in activating latent TGF-β from inactive ECM depots (6, 7). Through its conserved cysteine protease inhibitor motif, CystC binds and inactivates cathepsin B by forming a reversible, high affinity enzyme-inhibitor complex (8, 9). Independent of its effects on cathepsin B activity, CystC also regulates cell proliferation (10, 11), raising the possibility that CystC targets proteinase-dependent and -independent pathways.

Mutations in or altered expression of CystC has been linked to the development and progression of several human pathologies. For instance, a single point mutation in CystC causes Hereditary CystC Amyloid Angiopathy, a lethal autosomal dominant disease that results in massive cerebral hemorrhages in early adulthood (12). Moreover, altered CystC expression or serum enzyme-inhibitor levels are used as diagnostic markers for chronic renal insufficiencies (13), and for cancers of the lung, skin, colon, and myeloid compartment (3, 14-16). Thus, altered CystC concentrations within cell microenvironments have dire consequences leading to the development and progression of human diseases.

TGF-β is a multifunctional cytokine that governs cell growth and motility in part through its regulation of cell microenvironments, and thus plays a prominent role in regulating disease development in humans (17). Critical to regulation of cell microenvironments by TGF-β is its induction or repression of cytokines, growth factors, and ECM proteins by fibroblasts (17).

Transforming growth factor-β (TGF-β) is also a potent suppressor of mammary epithelial cell (MEC) proliferation, and as such, an inhibitor of mammary tumor formation. However, aberrant genetic and epigenetic events operant during tumorigenesis typically abrogate the cytostatic function of TGF-β, thereby contributing to tumor formation and progression. For example, malignant MECs typically evolve resistance to TGF-β-mediated growth arrest, thus enhancing their proliferation, invasion, and metastasis when stimulated by TGF-β. Recent findings suggest that therapeutics designed to antagonize TGF-β signaling may alleviate breast cancer progression, thereby improving the prognosis and treatment of breast cancer patients.

Oncogenic epithelial-mesenchymal transitions (EMT) comprise a complex array of gene expression and repression that elicits tumor metastasis in localized carcinomas (Thiery, 2002; Grunert et al., 2003). The acquisition of metastatic phenotypes by dedifferentiated tumors is the most lethal facet of cancer and the leading cause of cancer-related death (Yoshida et al., 2000; Fidler, 2002). Transforming growth factor-β (TGF-β) normally represses these processes by prohibiting epithelial cell proliferation, and by creating a cell microenvironment that inhibits epithelial cell motility, invasion, and metastasis (Blobe et al., 2000; Siegel, 2003). Carcinogenesis often subverts the tumor suppressing function of TGF-β, thereby endowing TGF-β with oncogenic activities that promote the growth and spread of developing tumors, including the initiation and stabilization of tumor EMT (Thiery, 2002; Grunert et al., 2003; Blobe et al., 2000; Siegel et al., 2003; Wakefield et al., 2002).

The duality of TGF-β to both suppress and promote cancer development was observed originally using transgenic TGF-β1 expression in mouse keratinocytes, which initially suppressed benign skin tumor formation prior to promoting malignant conversion and spindle cell carcinoma generation (Cui et al., 1996). More recently, TGF-β signaling was shown to inhibit the tumorigenicity of normal, premalignant, and malignant breast epithelial cells, while stimulating that of highly invasive and metastatic breast cancer cells (Tang et al., 2003). Fundamental gaps exist in the knowledge of how malignant cells overcome the cytostatic actions of TGF-β, and of how TGF-β stimulates the progression of developing tumors. Indeed, these knowledge gaps have prevented science and medicine from developing treatments effective in antagonizing TGF-β oncogenicity in progressing cancers, particularly those of the breast.

TGF-β is widely expressed during development to regulate the interactions between epithelial and mesenchymal cells, particularly those in the lung, kidney, and mammary gland. Inappropriate reactivation of EMT during tumorigenesis is now recognized as an important process necessary for tumor acquisition of invasive and metastatic phenotypes (Thiery, 2002; Grunert et al., 2003). By cooperating with oncogenes and growth factors, TGF-β potently induces EMT and serves to stabilize this transition via autocrine signaling. Moreover, these events appear to underlie TGF-β oncogenicity and its ability to promote cancer progression (Miettinen et al., 1994; Oft et al., 1998; Oft et al., 1996; Portella et al., 1998). Molecular dissection of TGF-β signaling systems necessary for its induction of EMT has clearly established a role for Smad2/3 in mediating EMT, particularly when coupled with signals emanating from oncogenic Ras (Piek et al., 1999; Oft et al., 2002; Janda et al., 2002). However, Smad2/3-independent signaling also has been implicated in TGF-β stimulation of EMT. For instance, TGF-β stimulates EMT in cancers of the breast and other tissues by activating PI-3-kinase, AKT, RhoA, p160(ROCK), and p38 MAPK (Janda et al., 2002; Bhowmick et al., 2001, Mol. Biol. Cell; Bhowmick et al., 2001, J. Biol. Chem.; Bakin et al., 2000; Yu et al., 2002) In addition, EMT in TGF-β treated MECs is abrogated by measures that inhibit β1 integrin activity (Bhowmick et al., 2001, J. Biol. Chem.), thus establishing the necessity of β1 integrin expression for EMT stimulated by TGF-β. Finally, by repressing Id2 and Id3 expression (Kowanetz et al., 2004), inducing Snail and SIP1 expression (Kang et al., 2004), and stimulating NF-κB activity (Huber et al., 2004), TGF-β regulates transcription factor activity operant in mediating the transition from epithelial to mesenchymal cell markers. Clearly, EMT and the mechanisms whereby TGF-β participates in this process involve a complex cascade of gene expression and repression, the magnitude of which remains to be elucidated fully.

Accordingly, although TGF-β clearly inhibits the growth and development of early stage tumors, an accumulating body of evidence implicates TGF-β signaling as a stimulus necessary for the metastasis and dissemination of late stage tumors (Blobe et al., 2000; Siegel, 2003). A comprehensive understanding of how TGF-β both suppresses and promotes tumorigenesis remains an unknown and fundamental question that directly impacts our ability to effectively target the TGF-β signaling system during treatment of human malignancies. Indeed, deciphering this paradox remains the most important question concerning the biological and pathological actions of this multifunctional cytokine The ability of TGF-β to induce cancer growth and metastasis suggests that developing therapeutics to antagonize and/or circumvent TGF-β signaling may prove effective in treating metastatic malignancies, perhaps by preventing TGF-β stimulation of EMT.

BRIEF DESCRIPTION OF THE FIGURES OF THE INVENTION

SUMMARY OF THE INVENTION

Figure 1A:
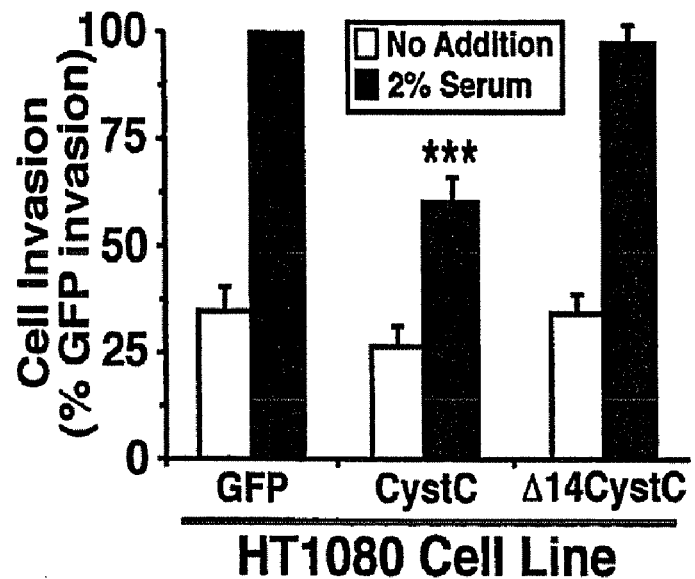
FIG. 1A is bar graph showing that CystC expression significantly inhibited HT1080 cell invasion through Matrigel matrices.

One embodiment of the present invention relates to an isolated Cystatin C homologue. The homologue comprises an amino acid sequence that is at least about 50% identical to, or about 60% identical to, or about 70% identical to, or about 80% identical to, or about 90% identical to, an amino acid sequence of a wild-type Cystatin C; and the homologue is less than 100% identical to, or less than about 95% identical to, or less than about 90% identical to, an amino acid sequence of a wild-type Cystatin C. The Cystatin C homologue inhibits TGF-β biological activity. In one aspect of the invention, the wild-type Cystatin C has an amino acid sequence represented by SEQ ID NO:2.

In one aspect of this embodiment, the amino acid sequence of the homologue differs from the amino acid sequence of the wild-type Cystatin C protein by a deletion, insertion, substitution or derivatization of at least one amino acid residue. In another aspect, the amino acid sequence of the homologue differs from the amino acid sequence of the wild-type Cystatin C protein by a disruption of the wild-type sequence sufficient to reduce or abolish the biological activity of the conserved cysteine proteinase inhibitor motif. For example, the wild-type Cystatin C protein can be represented by SEQ ID NO:2 and the conserved cysteine proteinase inhibitor motif can be located between about position 80 and about position 93 of SEQ ID NO:2. In another aspect, the amino acid sequence of the homologue differs from the amino acid sequence of the wild-type Cystatin C protein represented by SEQ ID NO:2 by a deletion of amino acid residues from about position 80 to about position 93 with reference to SEQ ID NO:2.

Another embodiment of the present invention relates to an isolated protein comprising a fragment of a wild-type Cystatin C protein that inhibits TGF-β biological activity. In one aspect, the protein inhibits the binding of TGF-β to its receptor, including but not limited to, TβRII. In one aspect, the fragment comprises at least about 100 amino acids, or at least about 75 amino acids, or at least about 55 amino acids, of the C-terminal portion of the wild-type Cystatin C protein. In another aspect, the fragment differs from the wild-type amino acid sequence by a deletion of at least about 10 amino acids, or at least about 20 amino acids, or at least about 50 amino acids, from the N-terminus of the wild-type protein.

Another embodiment of the invention relates to a composition, including a therapeutic composition, comprising any of the above-identified homologues or fragments and a pharmaceutically acceptable carrier.

Yet another embodiment of the present invention relates to a method to inhibit tumor malignancy or invasion, comprising administering to a tumor cell Cystatin C or a homologue or synthetic mimetic thereof having Cystatin C biological activity. In one aspect, the biological activity comprises inhibition of the binding of TGF-β to its receptor. In another aspect, the tumor malignancy is cathepsin B-mediated tumor cell malignancy, and the method comprises contacting a tumor cell with Cystatin C or a homologue or synthetic mimetic thereof having Cystatin C biological activity effective to inhibit the biological activity of cathepsin B in the tumor cell or in the microenvironment of the tumor cell. For example, the Cystatin C or homologue or synthetic mimetic thereof can inhibit the biological activity of extracellular cathepsin B. In another aspect, the tumor malignancy is TGF-β-mediated tumor malignancy, and the method comprises contacting a tumor cell with Cystatin C or a homologue or synthetic mimetic thereof effective to inhibit the biological activity of TGF-β in the tumor cell or in the microenvironment of the tumor cell. In yet another aspect, the Cystatin C or a homologue or synthetic mimetic thereof inhibits cathepsin B-mediated activation of TGF-β in the cell or tissue or in the microenvironment of the cell or tissue.

Another embodiment of the present invention relates to a method to inhibit tumor cell malignancy, comprising increasing the expression and/or biological activity of endogenous Cystatin C in tumor cells.

Yet another embodiment of the present invention relates to a method to inhibit TGF-β biological activity, comprising administering to a cell, tissue or patient Cystatin C or a homologue or synthetic mimetic thereof, or increasing the expression or biological activity of endogenous Cystatin C, in an amount effective to inhibit biological activity of TGF-β. In one aspect, the method is used to treat a patient with cancer. In another aspect, the method is used to treat a patient that has or is predisposed to develop metastatic cancer. In yet another aspect, the method is used to treat a patient that has a proliferative or fibrotic condition or disease mediated at least in part by TGF-β expression or activity.

Another aspect of the invention relates to a method to increase TGF-β activity, comprising inhibiting the ability of Cystatin C to regulate TGF-β activity. In one aspect, the method includes contacting a TGF-β receptor with a Cystatin C homologue that is a competitive inhibitor of Cystatin C. In another aspect, the method includes contacting a TβRII receptor with a Cystatin C homologue that is a competitive inhibitor of Cystatin C. In another aspect, the method includes contacting Cystatin C with a compound that reduces the ability of Cystatin C to bind to or activate TβRII. In yet another aspect, the compound is a soluble TβRII receptor with a decreased affinity for TGF-β that binds to Cystatin C. In another aspect, the compound binds to Cystatin C and inhibits the ability of Cystatin C to bind to TβRII. In another aspect, the compound does not inhibit the ability of Cystatin C to inhibit cysteine proteases. Such a compound can include, but is not limited to, an antibody, an antigen binding fragment of an antibody, or a binding partner.

Another embodiment of the present invention relates to a method to design an antagonist or inhibitor of TGF-β activity, comprising: (a) designing or identifying a putative antagonist compound based on the structure of Cystatin C; (b) synthesizing the compound; and (c) selecting compounds from (b) that inhibit the biological activity of TGF-β. In one aspect, step (a) comprises performing structure-based drug design with a model representing the structure of Cystatin C. In another aspect, the step of selecting comprises selecting compounds that inhibit the binding of TGF-β to its receptor. In one aspect, the step of selecting comprises selecting compounds that inhibit TGF-β-mediated tumor cell malignancy or invasion.

Yet another embodiment of the present invention relates to a method to identify proteins that are inhibitors of TGF-β, comprising: (a) identifying proteins that are structural homologues of Cystatin C; and (b) evaluating proteins from (a) that are capable of regulating the biological activity of TGF-β. In one aspect, step (a) comprises identifying structural homologues or fragments of Cystatin C using sequence analysis. In another aspect, the method of evaluating comprises detecting whether the protein of (a) inhibits the binding of TGF-β to its receptor. In one aspect, the step of selecting comprises selecting compounds that inhibit TGF-β-mediated tumor cell malignancy or invasion.

Another embodiment of the present invention relates to a method to identify a regulator of transforming growth factor β (TGF-β), comprising: (a) contacting a cell that expresses a TGF-β receptor and Cystatin C with a putative regulatory compound; (b) detecting the expression of Cystatin C in the cell; and (c) comparing the expression of Cystatin C after contact with the compound to the expression of Cystatin C before contact with the compound, wherein detection of a change in the expression of Cystatin C in the cells after contact with the compound as compared to before contact with the compound indicates that the compound is a putative regulator of TGF-β and TGF-β signal transduction.

DETAILED DESCRIPTION OF THE INVENTION

The present invention generally relates to the use of Cystatin C, and biologically active fragments, homologues and synthetic mimetics thereof, to regulate the biological activity of TGF-β and TGF-β signal transduction pathways. The present invention relates to various compositions comprising Cystatin C and biologically active fragments, homologues and synthetic mimetics thereof for use in therapeutic, diagnostic and drug screening methods. The present invention relates to the use of Cystatin C and biologically active fragments, homologues and synthetic mimetics thereof, to treat or prevent tumor malignancy, including tumor invasion, including tumor malignancy that is mediated by cathepsin-B or by TGF-β. The present invention relates to methods of regulating Cystatin C expression and/or activity (i.e., up- or down-regulate) to regulate (as an antagonist or an agonist) the biological activity of TGF-β or TGF-β signal transduction pathways (e.g., TGF-β receptor signal transduction and the expression, activation and/or biological activity of downstream genes regulated by TGF-β, as well as regulation of TBF-β receptors). In particular, such methods can be used to treat or ameliorate at least one symptom of a disease or condition in which TGF-β plays a role, including cancers and various proliferative and fibrotic conditions and diseases associated with TGF-β activity. The present invention also relates to the use of Cystatin C and biologically active fragments, homologues and synthetic mimetics thereof as lead compounds for the development of additional antagonists (or agonists) of TGF-β biological activity or of cathepsin-B biological activity. The present invention also relates to the identification of other members of the Cystatin C supergene family and/or the evaluation of such members for the ability to inhibit TGF-β, followed by the use of members identified as antagonists of TGF-β, including homologues, fragments and synthetic mimetics thereof, in any of the methods described for Cystatin C herein. The present invention also includes the use of inhibitors of Cystatin C to regulate the activity of TGF-β or to release the inhibition of Cystatin C on cysteine proteases (e.g., cathepsin B). The present invention can include regulation of any of the TGF-β isoforms (TGF-β1, TGF-β2 and/or TGF-β3) by Cystatin C and biologically active fragments, homologues and synthetic mimetics thereof. In one embodiment, the biological activity of TGF-β1 or TGF-β3 is inhibited. In another embodiment, the biological activity of TGF-β2 is inhibited. In yet another embodiment, the biological activity of any one of TGF-β1, TGF-β2 and/or TGF-β3 is regulated.

Herein the inventor shows that TGF-β stimulates CystC transcript and protein expression in murine 3T3-L1 fibroblasts. The inventor further shows that CystC is aberrantly downregulated in human tumors, and that its overexpression in highly malignant human HT1080 fibrosarcoma cells inhibits their invasion in a cathepsin B-dependent manner. Interestingly, CystC also inhibits HT1080 cell expression of TGF-β-responsive genes via a cathepsin B-independent mechanism. Invasion of 3T3-L1 cells proceeds through cathepsin B- and TGF-β-dependent pathways: CystC inhibits both pathways, while a CystC mutant (i.e., Δ14CystC) unable to inactivate cathepsin B selectively inhibits TGF-β-dependent invasion, suggesting that CystC targets proteinase-dependent and -independent signaling pathways. Accordingly, both CystC and Δ14CystC significantly reduce TGF-β-stimulated gene expression in 3T3-L1 cells by inhibiting the binding of TGF-β to its type II receptor (TβR-II). Collectively, the findings described herein establish a novel CystC-mediated feedback loop that inhibits TGF-β signaling, doing so by antagonizing TGF-β binding to TβR-II.

More specifically, cell microenvironments play an important role in regulating the physiology and homeostasis of cells, including their survival, proliferation, differentiation, and motility (35). TGF-β is a powerful tumor suppressor that prevents cancer development by inhibiting cell cycle progression, and by creating cell microenvironments that inhibit uncontrolled cell growth, invasion, and metastasis. During cancer progression, the tumor suppressing function of TGF-β is frequently subverted, thus transforming TGF-β from a suppressor of cancer formation to a promoter of its growth and metastasis (17, 24). Although mutations in the TGF-β signaling system occur during carcinogenesis and contribute to tumor formation by abrogating TGF-β-mediated cell cycle arrest (17, 24), these aberrances do not explain the paradoxical function of TGF-β to promote the proliferation, invasion, and metastasis of cancer cells previously liberated from its growth inhibitory actions. Alternatively, recent studies have established fibroblasts as instrumental intermediaries of tumor growth and metastasis stimulated by TGF-β. When activated by TGF-β, fibroblasts synthesize and secrete a variety of cytokines, growth factors, and ECM proteins into tumor:host microenvironments. These secretory proteins facilitate tumor:host cross-talk that ultimately promotes the induction, selection, and expansion of neoplastic cells by enhancing their growth, survival, and motility (36). The inventor therefore sought to identify these TGF-β-regulated fibroblast secretory proteins, and to determine their function in normal and cancerous cells.

The inventor now presents CystC as a novel gene target for TGF-β in 3T3-L1 fibroblasts. The inventor further shows that CystC expression is prominently downregulated in human cancers (see Example 2), and conversely, that augmenting CystC expression in highly malignant fibrosarcoma cells significantly reduced their invasion through synthetic basement membranes (FIG. 1). Most strikingly, these studies identified CystC as a novel antagonist of TGF-β signaling (FIGS. 1-3). Indeed, the inventor shows for the first time that CystC inhibits gene expression (FIGS. 1 and 3) and cellular invasion (FIG. 3) stimulated by TGF-β, doing so by antagonizing TGF-β binding to TβR-II (FIG. 4). Thus, the inventor's study defines a novel cathepsin B-independent function for CystC, and has potentially identified a novel CystC-mediated feedback loop designed to inhibit TGF-β signaling.

The inactivation of cathepsin B proteinase activity by CystC has been a focal point of numerous investigations aimed at understanding the invasive properties of cancer cells (19, 37, 38). Although it is generally accepted that extracellular cathepsin B mediates cancer cell invasion, a recent report by Szpaderska and Frankfater (20) has provided evidence to the contrary by demonstrating the importance of intracellular cathepsin B to cancer cell invasion of through Matrigel matrices. In contrast, the inventor shows herein that expression of CystC, and not Δ14CystC, significantly inhibited HT1080 cell invasion. Moreover, the cell permeable cathepsin B inhibitor, CA-074ME, failed to alter HT1080 cell invasion, whereas its cell impermeable counterpart, cathepsin B inhibitor II, fully recapitulated the inhibitory effect of CystC on HT1080 cell invasion. Thus, HT1080 cell invasion occurs predominantly via the proteinase activities of extracellular cathepsin B, which is subject to inactivation by CystC.

The present inventor's studies also provide the first evidence that 3T3-L1 cell invasion proceeds through a bifurcated signaling system coupled to the activation of cathepsin B and TGF-β signaling. Moreover, the differential abilities of CystC (i.e., both pathways) and Δ14CystC (i.e., TGF-β pathway) to inhibit 3T3-L1 cell invasion implicates CystC as key regulator not only of cathepsin B-mediated invasion, but also that mediated by TGF-β. Although the proteolytic pathways targeted by TGF-β in 3T3-L1 cells remain unknown, without being bound by theory, the present inventor suspects involvement of members of the matrix metalloproteinase family (e.g., MMP-2 and MMP-9) whose expression and activity are regulated by TGF-β (39). Studies exploiting the anti-TGF-β properties of Δ14CystC will facilitate the identification and dissection of this TGF-β-regulated invasive pathway. Indeed, both cathepsin B (19) and TGF-β (40) localize to invading face of highly malignant tumors. In addition to its role in cancer cell invasion, cathepsin B also mediates latent TGF-β activation (6, 7), and as such, would be predicted to enhance the tumor promoting effects of TGF-β. Based on these findings, the inventor proposes that measures designed to deliver CystC to developing tumors will reduce their malignancy by inhibiting (i) cathepsin B-mediated invasion, (ii) cathepsin B-mediated TGF-β activation, and (iii) TGF-β signal transduction.

The present inventor (Example 2) and others (3, 37) have found tumorigenesis to induce significant downregulation of CystC expression, consistent with a tumor suppressing function for CystC. Recently, mice deficient in CystC expression were generated and found to be viable and exhibit no pronounced abnormalities (41). In addition, no differences in the latency and growth of subcutaneous and intracerebral tumors were detected in wild-type and CystC-null mice. Quite surprisingly, lung colonization by cancer cells was suppressed in CystC-deficient mice as compared to their wild-type counterparts (41). Although the mechanism mediating this contradictory effect of CystC on cancer cell metastasis is currently unknown, the authors speculate that dysregulated cathepsin B activity suppresses metastasis by catabolizing local cytokines/growth factors necessary for metastatic cancer cell seeding and growth (41). Based on the present findings, the inventor instead proposes that CystC deficiency increases tonic TGF-β signaling, resulting in enhanced tumor suppression and the creation of cell microenvironments that fail to efficiently support the metastatic spread and seeding of cancer cells. Therefore, without being bound by theory, the inventor proposes that CystC deficiency may potentiate cellular response to TGF-β (i.e., via loss of CystC-mediated feedback loop).

Finally, the Type 3 cystatin family member, fetuin, has also been characterized as a TGF-β antagonist (27-29). Fetuin contains a 19 amino acid TRH1 domain (TGF-β receptor II homology 1; (29)) that interacts physically with TGF-β and prevents its binding to TGF-β receptors (29). Although CystC contains C-terminal 21 amino acid sequence having similarity to TRH1, the present inventor was unable to observe a direct physical interaction between TGF-β and CystC. In contrast, the inventor found that CystC inhibits the binding of TGF-β to TβR-II, both in live cells and in vitro. Interestingly, initial structure-function studies by the inventor have implicated the C-terminal domain of CystC in mediating its antagonism of TGF-β signaling. Given the identification of two CystC superfamily members capable of inhibiting TGF-β signaling, the inventor proposes that additional CystC superfamily members may similarly function to antagonize the activities of other TGF-β superfamily members, as well as the activities of other cytokines/growth factors. Importantly, the present inventor's findings give credence to future studies aimed at exploiting the anti-TGF-β properties of CystC (or Δ14CystC) to selectively inhibit the oncogenic activities of TGF-β. Indeed, CystC will form the basis for rationale drug design to facilitate the development of specific TGF-β receptor antagonists necessary to improve the therapeutic response of human malignancies, as well as a variety of proliferative and fibrotic diseases regulated by TGF-β.

Given these results, the inventor further tested the ability of CystC, as a novel TβR-II antagonist, to block the oncogenic activities of TGF-β, particularly its ability to stimulate epithelial-mesenchymal transition (EMT). More specifically, the present inventor tested the oncogenesis-inhibitory properties of CystC by measuring the ability of CystC to antagonize TGF-β oncogenicity in two established in vitro models of cancer progression: (i) EMT of normal murine NMuMG mammary epithelial cells (MEC), and (ii) morphological transformation and anchorage-independent growth of normal rat kidney fibroblasts (NRK). The present inventor demonstrates herein that CystC effectively and completely negated TGF-β stimulation of EMT and morphological transformation in mammary and kidney epithelial cells, respectively. Thus, by antagonizing TGF-β signaling and preventing its stimulation of EMT, CystC is believed to represent a novel TGF-β chemopreventive agent effective in neutralizing TGF-β oncogenicity and its stimulation of tumor metastasis.

More specifically, as described in the Examples in detail (see Examples 8 and 9), CystC and Δ14CystC (a CystC mutant impaired in its ability to inhibit cathepsin protease activity) both inhibited NMuMG cell EMT and invasion stimulated by TGF-β by preventing actin cytoskeletal rearrangements and E-cadherin downregulation. Moreover, both CystC molecules completely antagonized TGF-β-mediated morphological transformation and anchorage-independent growth of NRK cells, as well as inhibited their invasion through synthetic basement membranes. Therefore, the present inventor has shown that TGF-β stimulation of initiating metastatic events, including decreased cell polarization, reduced cell-cell contact, and elevated cell invasion and migration, are prevented completely by CystC treatment.

Accordingly, the inventor has demonstrated CystC and Δ14CystC both prevent EMT and morphological transformation stimulated by TGF-β, and thus propose these small molecules as innovative models for the development of novel TβR-II antagonists designed to combat TGF-β stimulation of tumor progression and EMT. The inventor further proposes that the chemopreventive effectiveness of CystC will be potentiated by its inhibition of cathepsin B-mediated invasion and metastasis (Turk et al., 2002; Yan et al., 2003; Turk et al., 2000; Roshy et al., 2003), and of cathepsin B-mediated activation of latent TGF-β (Somana et al., 2002; Guo et al., 2002; Gantt et al. 2003), which co-localizes with cathepsin B to the invading face of malignant tumors (Wakefield, 2001; Calkins et al., 1998; Sinha et al., 1995; Sameni et al., 2000). Moreover, CystC-mediated cathepsin B inactivation will reduce the activity of the urokinase plasminogen system, which enhances tumor cell extracellular matrix degradation, as well as growth factor and latent TGF-β activation (Choong et al., 2003). Cumulatively, the chemopreventive activities of CystC will antagonize cancer cell response to TGF-β by inhibiting TGF-β binding, as well as by reducing TGF-β bioavailability within tumor microenvironments, thereby alleviating TGF-β stimulation of EMT and tumor metastasis in late stage tumors.

In summary, the inventor demonstrated the effectiveness of CystC to inhibit MEC EMT and fibroblast morphological transformation stimulated by TGF-β. CystC antagonism of TGF-β signaling in MECs occurs independent of its inactivation of cathepsin protease activity, presumably via CystC:TβR-II complex formation and the prevention of TGF-β binding. The inventor proposes that CystC or its peptide mimetics ultimately hold the potential to improve the therapeutic response of human malignancies regulated by TGF-β, particularly cancers of the breast.

Also encompassed by the invention is the use of inhibitors of CystC to regulate the biological effects of CystC on TGF-β and/or cathepsin B.

It will be understood that this invention is not limited to the particular methodology, protocols, cell lines, animal species or genera, constructs, or reagents described herein, as such may vary. It is also to be understood that the terminology used herein is for the purpose of describing particular embodiments only, and is not intended to limit the scope of the invention that will be limited only by the appended claims. All technical and scientific terms used herein have the same meaning as commonly understood to one of ordinary skill in the art to which this invention belongs unless clearly indicated otherwise. Furthermore, to the extent that any of the following discussion is general or genetic, it can be applied to any of the proteins, nucleic acids, homologues, fragments and mimetics described herein, as well as to any of the methods described herein.

One embodiment of the present invention relates to Cystatin C proteins, and to homologues and mimetics thereof that are useful in one or more methods of the present invention, including any methods that take advantage of the ability of Cystatin C to regulate TGF-β activity by interfering with the ability of TGF-β to interact with its receptor. In particular, the present invention relates to homologues of Cystatin C, including both protein and synthetic homologues (also called mimetics) that have the biological activity of the wild-type Cystatin C protein, or that at least have the ability to regulate TGF-β activity by interfering with the ability of TGF-β to interact with its receptor. Compositions and formulations comprising such proteins and homologues are also encompassed by the invention, as well as methods of using such proteins and homologues.

As discussed above, Cystatin C (CystC) is a ubiquitously expressed, small molecular weight (~16 kDa) secretory protein that preferentially inactivates cathepsin B, a cysteine proteinase implicated in stimulating cancer cell invasion and metastasis, and in activating latent TGF-β from inactive ECM depots. Through its conserved cysteine protease inhibitor motif, CystC binds and inactivates cathepsin B by forming a reversible, high affinity enzyme-inhibitor complex. Also, as demonstrated herein, CystC inhibits gene expression and cellular invasion stimulated by TGF-β, doing so by antagonizing TGF-β binding to TβR-II. The nucleotide and amino acid sequences for Cystatin C from a variety of animal species are known in the art. For example, the cDNA nucleotide sequence encoding human Cystatin C is found in NCBI Database GI No. 19882253 and is represented herein by SEQ ID NO:1. SEQ ID NO:1 encodes the human Cystatin C amino acid sequence represented herein by SEQ ID NO:2. The cDNA nucleotide sequence encoding murine Cystatin C is found in NCBI Database GI No. 31981821 and is represented herein by SEQ ID NO:3. SEQ ID NO:3 encodes the murine Cystatin C amino acid sequence represented herein by SEQ ID NO:4. The cDNA nucleotide sequence encoding rat Cystatin C is found in NCBI Database GI No. 34858909 and is represented herein by SEQ ID NO:5. SEQ ID NO:5 encodes the rat Cystatin C amino acid sequence represented herein by SEQ ID NO:6. The cDNA nucleotide sequence encoding bovine Cystatin C is found in NCBI Database GI No. 27806674 and is represented herein by SEQ ID NO:7. SEQ ID NO:7 encodes the bovine Cystatin C amino acid sequence represented herein by SEQ ID NO:8. The cDNA nucleotide sequence encoding rhesus monkey Cystatin C is found in NCBI Database GI No. 2281118 and is represented herein by SEQ ID NO:9. SEQ ID NO:9 encodes the rhesus monkey Cystatin C amino acid sequence represented herein by SEQ ID NO:10. There is a high degree of homology among Cystatin C proteins from these various animal species. For example, the murine, rat, bovine and rhesus monkey amino acid sequences are about 67%, 68%, 68%, and 97% identical, respectively, to the human Cystatin C amino acid sequence over the full length of such sequences. Human Cystatin C has been crystallized and the structure determined, and the atomic coordinates for the tertiary structure of Cystatin C is found in the Protein Database Accession No. 1G96 (described in and deposited by Janowski et al., *Nat. Struct. Biol.* 8(4):316-320, 2001), incorporated herein by reference in its entirety.

An isolated protein, according to the present invention, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. Reference to a particular protein from a specific organism, such as a "human Cystatin C protein", by way of example, refers to a Cystatin C protein (including a homologue of a naturally occurring Cystatin C protein) from a human or a Cystatin C protein that has been otherwise produced from the knowledge of the structure (e.g., sequence) of a naturally occurring Cystatin C protein from a human. In other words, a human Cystatin C protein includes any Cystatin C protein that has the structure and function of a naturally occurring Cystatin C protein from a human or that has a structure and function that is sufficiently similar to a human Cystatin C protein such that the Cystatin C protein is a biologically active (i.e., has biological activity) homologue of a naturally occurring Cystatin C protein from a human. As such, a human Cystatin C protein can include purified, partially purified, recombinant, mutated/modified and synthetic proteins.

In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

According to the present invention, Cystatin C biological activity can include one or more (or all) of the following biological activities of wild-type Cystatin C: inhibition of a cysteine protease, and particularly cathepsin B (e.g., by binding to and inactivating cathepsin B by forming a reversible, high affinity enzyme-inhibitor complex); regulation of cell proliferation; binding to a TGF-β receptor (e.g., binding to TβRII and thereby preventing TGF-β activation of TβRII); and inhibition of TGF-β stimulation of initiating metastatic events, including decreased cell polarization, reduced cell-cell contact, and elevated cell invasion and migration. According to the present invention, CystC biological activity can include the regulation of the activity of any isoform of TGF-β, including TGF-β1, TGF-β2 and TGF-β3. Similarly, CystC biological activity can include antagonizing the binding if TGF-β to any receptor of a TGF-β protein, including, but not limited to, TβR-I, TβR-II, and TβR-III. The present inventor believes, without being bound by theory, that CystC can antagonize TGF-β binding by binding more specifically to TβRII, and particularly to the extracellular ligand binding domain of TβRII, but the effect can include inhibition of any of the three receptors mentioned above.

Methods of detecting and measuring protein expression and biological activity include, but are not limited to, measurement of transcription of a protein, measurement of translation of a protein, measurement of posttranslational modification of a protein, measurement of the ability of the protein to bind to another protein(s); measurement of the ability of the protein to induce or participate in a particular biological effect (e.g., for Cystatin C, inhibition of the activity cathepsin B, inhibition of the binding of TGF-β to TβRII, regulation of cellular proliferation, inhibition of TGF-β and/or cathepsin B-dependent tumor cell malignancy and invasion). It is noted that an isolated protein of the present invention (including a homologue) is not necessarily required to have the biological activity of the wild-type protein. For example, a protein can be a truncated, mutated or inactive protein, for example. Such proteins are useful in screening assays or diagnostic assays, for example, or for other purposes such as antibody production. In a preferred embodiment, the isolated proteins of the present invention have a biological activity that is similar to that of the wild-type protein (although not necessarily equivalent, as discussed below).

Methods to measure protein expression levels generally include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microarray, microscopy, fluorescence activated cell sorting (FACS), and flow cytometry, as well as assays based on a property of the protein including but not limited to enzymatic activity or interaction with other protein partners. Binding assays are also well known in the art. For example, a BIAcore machine can be used to determine the binding constant of a complex between two proteins. The dissociation constant for the complex can be determined by monitoring changes in the refractive index with respect to time as buffer is passed over the chip (O'Shannessy et al. Anal. Biochem. 212:457-468 (1993); Schuster et al., Nature 365:343-347 (1993)). Other suitable assays for measuring the binding of one protein to another include, for example, immunoassays such as enzyme linked immunoabsorbent assays (ELISA) and radioimmunoassays (RIA); or determination of binding by monitoring the change in the spectroscopic or optical properties of the proteins through fluorescence, UV absorption, circular dichroism, or nuclear magnetic resonance (NMR).

Methods suitable for use in measuring the biological activity of Cystatin C or homologues and mimetics thereof of the invention include, but are not limited to: binding assays (described above and in the Examples) for CystC binding to cathepsin C, to another cysteine protease, or to TβRII; assays for measuring the effect of CystC on cysteine protease activity (e.g., enzyme assays); assays for measuring the effect of CystC on gene expression (e.g., Northern blot, Western blot, microarray studies); assays for measuring the effect of CystC on TGF-β activity (e.g., reporter gene assays, proliferation assays, receptor binding assays, immunofluorescence assays); assays for measuring the effect of CystC on tumor cell malignancy and invasion (e.g., tumor cell invasion assays, soft agar assays, morphological analyses, immunofluorescence assays). Other assays for CystC biological activity based on the disclosure provided herein will be apparent to those of skill in the art. A variety of different assays for determining and measuring the activity of CystC and homologues thereof is described in the Examples.

The present invention includes homologues of various proteins described herein (e.g., Cystatin C protein). As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. Preferred homologues of a Cystatin C protein are described in detail below. It is noted that homologues can include synthetically produced homologues (synthetic peptides or proteins), naturally occurring allelic variants of a given protein, or homologous sequences from organisms other than the organism from which the reference sequence was derived.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, J. Mol. Biol. (1982) 157: 105-132), or on the basis of the ability to assume similar polypeptide secondary structure (Chou and Fasman, Adv. Enzymol. (1978) 47: 45-148, 1978).

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications or mutations in protein homologues, as compared to the wild-type protein, either increase, decrease, or do not substantially change, the basic biological activity of the homologue as compared to the naturally occurring (wild-type) protein. With regard to Cystatin C, the present invention includes homologues that maintain the basic biological activities of the wild-type protein, as well as homologues that maintain only some of the biological activities of the wild-type protein (e.g., the ability to regulate TGF-β activity, but not cathepsin B activity). An example of such a homologue is described in the Examples (i.e., the Δ14CystC modified protein). Biological activities of Cystatin C have been described in detail elsewhere herein. Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same general biological activity as the wild-type protein, but at a reduced or increased level of activity as compared to the wild-type protein. A functional domain of a Cystatin C protein is a domain (i.e., a domain can be a portion of a protein) that is capable of performing a biological function (i.e., has biological activity, such as the ability to bind to a TGF-β receptor, including TβRII).

In one preferred embodiment of the present invention a CystC homologue has an amino acid sequence that differs from the amino acid sequence of the wild-type Cystatin C protein by a disruption (e.g., deletion, substitution, insertion) of the wild-type sequence sufficient to reduce or abolish the biological activity of the conserved cysteine proteinase inhibitor motif. According to the present invention, the conserved cysteine proteinase inhibitor motif of human CystC, for example, is located between about position 80 and about position 93 of CystC. In one aspect, the amino acid sequence of the homologue differs from the amino acid sequence of the wild-type Cystatin C protein by a deletion of amino acid residues from about position 50 to about position 120 with reference to the wild-type amino acid sequence of human CystC. In another aspect, the amino acid sequence of the homologue differs from the amino acid sequence of the wild-type Cystatin C protein by a deletion of amino acid residues from about position 60 to about position 110, or from about position 70 to about position 100, or from about position 80 to about position 93, with reference to the wild-type amino acid sequence of human CystC. Also encompassed are any length deletions between about position 50 and 120 that include the about position 80 to about position 93 deletion, with reference to the human Cyst C amino acid sequence (SEQ ID NO:2). A human CystC having a deletion from position 80 to position 93 is described in the Examples and referred to herein as Δ14CystC. Δ14CystC does not bind to cathepsin B and therefore does not have the cysteine protease inhibitory activity of wild-type CystC. However, Δ14CystC retains the ability to regulate the activity of TGF-β comparable to the wild-type protein. Such activity (or lack thereof) can be used to evaluate other deletion mutants of CystC as described above. The corresponding positions in other CystC proteins from other species can readily be determined by one of skill in the art, for example, by alignment of the human sequence with the other sequence (described elsewhere herein). With regard to the TGF-β-regulating activity of CystC, the present inventor has determined that this activity is correlated with residues in the C-terminal region of CystC. Therefore, a CystC homologue of the invention (including a biologically active fragment thereof) preferably retains the C-terminal portion of the wild-type protein, and most preferably, at least the last 50 C-terminal amino acids, or at least the last 45 C-terminal amino acids, or at least the last 40 C-terminal amino acids, or at least the last 35 C-terminal amino acids, or at least the last 30 C-terminal amino acids, or at least the last 25 C-terminal amino acids, and preferably at least the last 21 C-terminal amino acids of the wild-type sequence. The retention of the TGF-β-regulating activity of a CystC homologue can readily be evaluated, for example, by determining whether the homologue can bind to a TGF-β receptor such as TβRII (described herein).

In one embodiment of the invention, a homologue of CystC useful in the methods of the invention includes a fragment of the full-length Cyst C. In one embodiment, such a fragment consists essentially of or consists of a fragment of a wild-type Cystatin C protein that is capable of inhibiting TGF-β biological activity. In one embodiment, the fragment differs from the wild-type amino acid sequence by a deletion of at least about 10 amino acids from the N-terminus of the wild-type protein, or a deletion of at least about 15 amino acids from the N-terminus, or a deletion of at least about 20 amino acids from the N-terminus, or a deletion of at least about 25 amino acids from the N-terminus, or a deletion of at least about 30 amino acids from the N-terminus, or a deletion of at least about 35 amino acids from the N-terminus, or a deletion of at least about 40 amino acids from the N-terminus, or a deletion of at least about 45 amino acids from the N-terminus, or a deletion of at least about 50 amino acids from the N-terminus, or a deletion of at least about 55 amino acids from the N-terminus, or a deletion of at least about 60 amino acids from the N-terminus, or a deletion of at least about 65 amino acids from the N-terminus, or a deletion of at least about 70 amino acids from the N-terminus, or a deletion of at least about 80 amino acids from the N-terminus, or a deletion of at least about 85 amino acids from the N-terminus, or a deletion of at least about 90 amino acids from the N-terminus, or a deletion of at least about 95 amino acids from the N-terminus, or a deletion of at least about 100 amino acids from the N-terminus of the wild-type CystC protein.

In one aspect of the invention, a homologue of CystC comprises, consists essentially of, or consists of, an amino acid sequence that is at least about 50% identical, and more preferably at least about 55% identical, and more preferably at least about 60% identical, and more preferably at least about 65% identical, and more preferably at least about 70% identical, and more preferably at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical (or any percentage between 60% and 99%, in whole single percentage increments) to the natural reference amino acid sequence (e.g., the wild-type CystC protein, such as that represented by SEQ ID NO:2, SEQ ID NO:4, SEQ ID NO:6, SEQ ID NO:8 or SEQ ID NO:10) over a length of the natural sequence that is at least the same as the length of the homologue. A homologue includes a fragment of a natural (full-length or wild-type sequence), including biologically active, partially biologically active (e.g., binds to a ligand or receptor, but may not have further biological activity), biologically inactive, and soluble forms of the natural protein (e.g., if the natural protein is a membrane or insoluble protein).

In one embodiment, a CystC homologue of the present invention comprises, consists essentially of, or consists of an amino acid sequence that is less than 100% identical to the wild-type sequence for CystC, or less than about 99% identical, or less than 98% identical, or less than 97% identical, or less than 96% identical, or less than 95% identical, or less than 94% identical, or less than 93% identical, or less than 92% identical, or less than 91% identical, or less than 90% identical to the wild-type CystC sequence (e.g., SEQ ID NO:2, SEQ ID NO:4, SEQ ID NO:6, SEQ ID NO:8 or SEQ ID NO:10), and so on, in increments of whole integers. The isolated CystC homologue of the present invention preferably has at least one biological activity of a naturally occurring or wild-type CystC protein.

As used herein, unless otherwise specified, reference to a percent (%) identity refers to an evaluation of homology which is performed using a BLAST homology search. BLAST homology searches can be performed using the BLAST database and software, which offers search programs including: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääeffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
   Reward for match=1
   Penalty for mismatch=-2
   Open gap (5) and extension gap (2) penalties
   gap x_dropoff (50) expect (10) word size (11) filter (on)
For blastp, using 0 BLOSUM62 matrix:
   Open gap (11) and extension gap (1) penalties
   gap x_dropoff (50) expect (10) word size (3) filter (on).

In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs, although for the direct comparison of two sequences, BLAST 2 is preferred.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, an isolated protein of the present invention, including an isolated homologue, includes a protein having an amino acid sequence that is sufficiently similar to a naturally occurring protein amino acid sequence that a nucleic acid sequence encoding the homologue is capable of hybridizing under moderate, high, or very high stringency conditions (described below) to (i.e., with) a nucleic acid molecule encoding the naturally occurring protein (i.e., to the complement of the nucleic acid strand encoding the naturally occurring protein amino acid sequence). A "complement" of nucleic acid sequence encoding a protein of the present invention refers to the nucleic acid sequence of the nucleic acid strand that is complementary to the strand which encodes the protein. Methods to deduce a complementary sequence are well known to those skilled in the art. It should be noted that since amino acid sequencing and nucleic acid sequencing technologies are not entirely error-free, the sequences presented herein, at best, represent apparent sequences of PUFA PKS domains and proteins of the present invention.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, low stringency hybridization and washing conditions, as referred to herein, refer to conditions which permit isolation of nucleic acid molecules having at least about 50% nucleic acid sequence identity with the nucleic acid molecule being used to probe in the hybridization reaction (i.e., conditions permitting about 50% or less mismatch of nucleotides). Moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M $Na^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M $Na^+$) at a temperature of between about 30° C. and about 45°

C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Proteins of the present invention also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of the membrane protein, or genes having signal sequences removed which are poorly tolerated in a particular recombinant host).

The present invention also includes a fusion protein or a chimeric protein that includes a desired protein-containing domain (e.g., CystC or a homologue or fragment thereof) attached to one or more fusion segments or additional proteins or peptides. Suitable fusion segments for use with the present invention include, but are not limited to, segments that can: enhance a protein's stability; provide other desirable biological activity; and/or assist with the purification of a protein (e.g., by affinity chromatography), or provide another protein function (e.g., as in a chimeric protein). A suitable fusion segment can be a domain of any size that has the desired function (e.g., imparts increased stability, solubility, action or biological activity; simplifies purification of a protein; or provides the additional protein function). Fusion segments can be joined to amino and/or carboxyl termini of the domain of the desired protein and can be susceptible to cleavage in order to enable straight-forward recovery of the protein. In one embodiment a suitable fusion segment or protein with which a chimeric or fusion protein can be produced is an antibody fragment and particularly, the Fc portion of an immunoglobulin protein. Any fusion or chimera partner that enhances the stability or half-life of CystC in vivo, for example, is contemplated for use in the present invention.

In one embodiment of the present invention, any of the above-described amino acid sequences, as well as homologues of such sequences, can be produced with from at least one, and up to about 20, additional heterologous amino acids flanking each of the C- and/or N-terminal end of the given amino acid sequence. The resulting protein or polypeptide can be referred to as "consisting essentially of" a given amino acid sequence. According to the present invention, the heterologous amino acids are a sequence of amino acids that are not naturally found (i.e., not found in nature, in vivo) flanking the given amino acid sequence or which would not be encoded by the nucleotides that flank the naturally occurring nucleic acid sequence encoding the given amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a given amino acid sequence that can be flanked by from at least one, and up to as many as about 60, additional heterologous nucleotides at each of the 5' and/or the 3' end of the nucleic acid sequence encoding the given amino acid sequence. The heterologous nucleotides are not naturally found (i.e., not found in nature, in vivo) flanking the nucleic acid sequence encoding the given amino acid sequence as it occurs in the natural gene.

The minimum size of a protein and/or a homologue or fragment thereof of the present invention is, in one aspect, a size sufficient to have the requisite biological activity, or sufficient to serve as an antigen for the generation of an antibody or as a target in an in vitro assay. In one embodiment, a protein of the present invention is at least about 8 amino acids in length (e.g., suitable for an antibody epitope or as a detectable peptide in an assay), or at least about 25 amino acids in length, or at least about 30 amino acids in length, or at least about 35 amino acids in length, or at least about 40 amino acids in length, or at least about 50 amino acids in length, or at least about 60 amino acids in length, or at least about 65 amino acids in length, or at least about 70 amino acids in length, or at least about 75 amino acids in length, or at least about 80 amino acids in length, or at least about 85 amino acids in length, or at least about 90 amino acids in length, or at least about 95 amino acids in length, or at least about 100 amino acids in length, or at least about 105 amino acids in length, or at least about 110 amino acids in length, or at least about 115 amino acids in length, or at least about 120 amino acids in length, or at least about 125 amino acids in length, or at least about 130 amino acids in length, or at least about 140 amino acids in length, or at least about 145 amino acids in length, and so on, in any length between 8 amino acids and up to the full length of a protein of the invention or longer, in whole integers (e.g., 8, 9, 10, . . . 25, 26, . . . 102, 103, . . . ). There is no limit, other than a practical limit, on the maximum size of such a protein in that the protein can include a portion of a protein, a functional domain, or a biologically active or useful fragment thereof, or a full-length protein, plus additional sequence (e.g., a fusion protein sequence), if desired.

Another embodiment of the present invention relates to a composition comprising at least about 500 ng, and preferably at least about 1 µg, and more preferably at least about 5 µg, and more preferably at least about 10 µg, and more preferably at least about 25 µg, and more preferably at least about 50 µg, and more preferably at least about 75 µg, and more preferably at least about 100 µg, and more preferably at least about 250 µg, and more preferably at least about 500 µg, and more preferably at least about 750 µg, and more preferably at least about 1 mg, and more preferably at least about 5 mg, of an isolated CystC protein or homologue or mimetic thereof comprising any of the CystC proteins or homologues thereof discussed herein. Such a composition of the present invention can include any carrier with which the protein is associated by virtue of the protein preparation method, a protein purification method, or a preparation of the protein for use in an in vitro, ex vivo, or in vivo method according to the present invention. For example, such a carrier can include any suitable excipient, buffer and/or delivery vehicle, such as a pharmaceutically acceptable carrier (discussed below), which is suitable for combining with the CystC protein of the present invention so that the protein can be used in vitro, ex vivo or in vivo according to the present invention.

Homologues of a protein described herein such as CystC homologues, including peptide and non-peptide agonists and antagonists of CystC, can be products of drug design or selection and can be produced using various methods known in the art. Such homologues can more particularly be referred to as mimetics. A mimetic refers to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art. Various methods of drug design, useful to design or select mimetics or other therapeutic compounds useful in the present invention are disclosed in Maulik et al., 1997, Molecular Biotechnology: Therapeutic Applications and Strategies, Wiley-Liss, Inc., which is incorporated herein by reference in its entirety.

An agonist can be any compound which is capable of mimicking, duplicating or approximating the biological activity of a naturally occurring or specified protein, for example, by associating with (e.g., binding to) or activating a protein (e.g., a receptor) to which the natural protein binds, so that activity that would be produced with the natural protein is stimulated, induced, increased, or enhanced. For example, an agonist can include, but is not limited to, a protein, compound, or an antibody that selectively binds to and activates or increases the activation of a receptor bound by the natural protein, other homologues of the natural protein, and any suitable product of drug design that is characterized by its ability to agonize (e.g., stimulate, induce, increase, enhance) the biological activity of a naturally occurring protein.

An antagonist refers to any compound or agent which is capable of acting in a manner that is antagonistic (e.g., against, a reversal of, contrary to) to the action of the natural agonist, for example by interacting with another protein or molecule in a manner that the biological activity of the naturally occurring protein or agonist is decreased (e.g., reduced, inhibited, blocked). Such a compound can include, but is not limited to, an antibody that selectively binds to and blocks access to a protein by its natural ligand, or reduces or inhibits the activity of a protein, a product of drug design that blocks the protein or reduces the biological activity of the protein, an anti-sense nucleic acid molecule that binds to a nucleic acid molecule encoding the protein and prevents expression of the protein, a ribozyme that binds to the RNA and prevents expression of the protein, and a soluble protein, which competes with a natural receptor or ligand.

A mimetic, including agonists and antagonists, can be produced using various methods known in the art. A mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

One embodiment of the present invention relates to isolated nucleic acid molecules comprising, consisting essentially of, or consisting of nucleic acid sequences that encode any of the proteins described herein, including a homologue or fragment of any of such proteins, as well as nucleic acid sequences that are fully complementary thereto. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on the biological activity of the protein as described herein. Protein homologues (e.g., proteins encoded by nucleic acid homologues) have been discussed in detail above.

A nucleic acid molecule homologue can be produced using a number of methods known to those skilled in the art (see, for example, Sambrook et al., *Molecular Cloning: A Laboratory Manual*, Cold Spring Harbor Labs Press, 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to encode a protein having the desired biological activity, or sufficient to form a probe or oligonucleotide primer that is capable of forming a stable hybrid with the complementary sequence of a nucleic acid molecule encoding the natural protein (e.g., under moderate, high or very high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence or a nucleic acid sequence encoding a full-length protein.

One embodiment of the present invention is a recombinant nucleic acid molecule comprising an isolated nucleic acid molecule of the present invention. According to the present invention, a recombinant nucleic acid molecule includes at least one isolated nucleic acid molecule of the present invention that is linked to a heterologous nucleic acid sequence. Such a heterologous nucleic acid sequence is typically a recombinant nucleic acid vector (e.g., a recombinant vector) which is suitable for cloning, sequencing, and/or otherwise manipulating the nucleic acid molecule, such as by expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. As used herein, the phrase "recombinant nucleic acid molecule" is used primarily to refer to a recombinant vector into which has been ligated the nucleic acid sequence to be cloned, manipulated, transformed into the host cell (i.e., the insert).

In one embodiment, a recombinant vector of the present invention is an expression vector, such that the recombinant nucleic molecule produced by inserting a nucleic acid molecule into the vector can be used to express, or produce the protein encoded by the nucleic acid molecule insert. As used herein, the phrase "expression vector" is used to refer to a vector that is suitable for production of an encoded product (e.g., a protein of interest). More particularly, a nucleic acid sequence encoding the product to be produced is inserted into the recombinant vector to produce a recombinant nucleic acid molecule. The nucleic acid sequence encoding the protein to be produced is inserted into the vector in a manner that operatively links the nucleic acid sequence to regulatory sequences in the vector (e.g., expression control sequences) which enable the transcription and translation of the nucleic acid sequence when the recombinant molecule is introduced into a host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete or inactivate an endogenous gene within the host cell (i.e., used for targeted gene disruption or knock-out technology) and/or to insert or replace a new, exogenous gene or nucleic acid molecule into the genome of the host cell.

According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell into which the recombinant nucleic acid molecule is to be introduced.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with a protein of the present invention or any heterologous signal segment capable of directing the secretion of a protein according to the present invention.

One or more recombinant molecules of the present invention can be used to produce an encoded product of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

In one embodiment, a protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a protein of the present invention. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes, such as the periplasmic space in E. coli; or be retained on the outer surface of a cell or viral membrane. The phrase "recovering the protein" refers to collecting the whole culture medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with the protein when it is used in a method disclosed by the present invention. Such methods include antibody production, agonist/antagonist identification assays, preparation of therapeutic compositions, administration in a therapeutic composition, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the protein comprises at least about 80% weight/weight of the total protein in a given composition, and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

One embodiment of the present invention relates to an antibody or antigen binding fragment that selectively binds to a protein of the present invention (e.g., Cystatin C protein). Such an antibody can selectively bind to any of the described herein, including fragments and other homologues of such receptors. According to the present invention, the phrase "selectively binds to" refers to the ability of an antibody, antigen binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to a given protein; and (b) a second portion which binds to a cell surface molecule expressed by a cell which expresses the protein. In this embodiment, the second portion can bind to any cell surface molecule. In a preferred embodiment, the second portion is capable of targeting the regulatory antibody to a specific target cell (i.e., the regulatory antibody binds to a target molecule). For example, the second portion of the bi-specific antibody can be an antibody that binds to another cell surface molecule on a target cell, such as a tumor cell.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

The invention also extends to non-antibody polypeptides, sometimes referred to as binding partners, that have been designed to bind specifically to, and either activate or inhibit as appropriate, a CystC protein or another protein (e.g., a TβRII). Examples of the design of such polypeptides, which possess a prescribed ligand specificity are given in Beste et al. (*Proc. Natl. Acad. Sci.* 96:1898-1903, 1999), incorporated herein by reference in its entirety.

One embodiment of the present invention includes an antibody, antigen-binding fragment thereof, or binding partner that binds to CystC and inhibits at least one biological activity of the CystC. For example, a preferred embodiment of the invention comprises an antibody, antigen-binding fragment thereof, or binding partner that selectively binds to CystC (e.g., in the C-terminal region of CystC), and inhibits the TGF-β-regulating portion of CystC, but not the cysteine protease inhibitory activity of CystC. The opposite embodiment (inhibition of the cysteine protease inhibitory activity but not the TGF-β regulatory activity) is also encompassed.

Another embodiment of the invention includes any CystC antagonist or inhibitor of CystC that results in a decrease in at least one biological activity of CystC as described herein. Such inhibitors include, but are not limited to, antibodies, antigen-binding fragments, binding partners, or other compounds (all described above) that selectively bind to and block or inhibit at least one biological activity of Cyst C (e.g., ability to bind to a TGF-β receptor, ability to activate a TGF-β receptor, ability to inhibit a cysteine protease, etc.); soluble TGF-β receptors and homologues thereof; CystC antagonists (including protein and non-protein homologues or mimetics) that are competitive inhibitors of natural CystC; and compounds that inhibit the expression of CystC. In one embodiment, a soluble TGF-β receptor is preferably a soluble TβRII receptor, and more preferably, a soluble TβRII receptor that has been modified to have decreased binding affinity for TGF-β and normal or increased binding affinity for CystC. Soluble TβRII are known in the art (e.g., see Examples), and can be modified based on the information provided herein to have the desired binding activity.

Some embodiments of the present invention include a composition or formulation comprising CystC or a fragment or homologue thereof (including agonists, antagonists, and other mimetics) or a regulator thereof for diagnostic, screening or therapeutic purposes. Therefore, another embodiment of the invention relates to a composition comprising a compound selected from: (i) an isolated CystC protein, fragment or homologue thereof (including agonists and antagonists that are proteins); (ii) a CystC agonist or antagonist compound other than a protein CystC homologue (e.g., a product of drug design); (iii) an isolated nucleic acid sequence encoding CystC or a homologue thereof, or (iv) a compound that affects the expression of an endogenous CystC gene in a cell. The composition typically also includes a pharmaceutically acceptable carrier. In this aspect of the present invention, an isolated CystC protein can be any of the CystC proteins previously described herein, including, but not limited to, a wild-type CystC protein, a CystC protein homologue, a fragment of CystC and/or a CystC fusion protein. Agonists and antagonists of CystC have also been described above. Isolated nucleic acid molecules encoding CystC or a homologue, fragment or fusion protein of CystC have also been described. In one embodiment, a composition of the present invention includes a combination of at least two of any of the above-identified compounds. The compositions and their components can be used in any of the diagnostic or therapeutic embodiments of the invention described herein.

A composition, and particularly a therapeutic composition, of the present invention generally includes a carrier, and preferably, a pharmaceutically acceptable carrier. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. Preferred pharmaceutically acceptable carriers are capable of maintaining a protein, compound, or nucleic acid molecule according to the present invention in a form that, upon arrival of the protein, compound, or nucleic acid molecule at the cell target in a culture or in patient, the protein, compound or nucleic acid molecule is capable of interacting with its target.

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), a drug, an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes and antibodies. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type, such as a tumor cell. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

Another delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

One embodiment of the present invention is to use the CystC proteins, homologues, mimetics and related TGF-β-regulatory compounds described herein, either alone, or in a composition for the regulation of TGF-β activity and/or the regulation of cathepsin B activity (including the regulation of TGF-β by cathepsin B). Regulation of TGF-β activity can include inhibition of TGF-β activity and enhancement of TGF-β activity. In embodiments where TGF-β activity is inhibited, such methods can be extended to methods to inhibit tumor malignancy (including metastatic malignancy) or a proliferative or fibrotic condition or disease, and particularly tumor malignancies or proliferative or fibrotic conditions or diseases that are mediated at least in part by TGF-β expression or activity, and/or by cathepsin-B regulation of TGF-β expression or activity. Methods involving the inhibition of TGF-β activity generally comprise administering to a patient or alternatively, contacting a cell (isolated or in vivo), with Cystatin C or a homologue or synthetic mimetic thereof having Cystatin C biological activity, or with a composition comprising such agents. When the cell is a tumor cell or the patient has cancer, the agent preferably is administered in an amount effective to inhibit the biological activity of cathepsin B and/or TGF-β activity in the tumor cell or in the microenvironment of the tumor cell. In one embodiment, the agent inhibits the biological activity of extracellular cathepsin B. In embodiments where the TGF-β inhibitory activity of CystC is to be decreased, the method includes administering to a patient or cell an inhibitor of CystC or Cyst antagonist, as described above.

In a related embodiment, the invention includes a method to increase the expression and/or biological activity of endogenous Cystatin C in a host cell, and particularly, a tumor cell. This method includes the step of administering a compound or composition that increases the expression or activity of CystC that is endogenously expressed by a host cell. Such compounds can be identified using the methods of identification of regulatory compounds described below. Another embodiment includes a method to decrease the expression and/or biological activity of endogenous CystC in a host cell, which includes administering a compound or composition that decreases the expression or activity of endogenous CystC.

A composition which includes a regulatory compound or agent or protein of the invention can be delivered to a cell culture or patient by any suitable method. Selection of such a method will vary with the type of compound being administered or delivered (i.e., protein, nucleic acid, mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site.

Administration routes include in vivo, in vitro and ex vivo routes. In vivo routes include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, subcutaneous administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In a preferred embodiment of the present invention, a composition is administered by a parenteral route (e.g., subcutaneous, intradermal, intravenous, intramuscular and intraperitoneal routes). Intravenous, intraperitoneal, intradermal, subcutaneous and intramuscular administrations can be performed using methods standard in the art. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for suppressing graft rejection by, for example, injecting the composition into the transplanted tissue, or for site-specific administration of a compound, such as at the site of a tumor.

Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell and/or target protein.

Various methods of administration and delivery vehicles disclosed herein have been shown to be effective for delivery of a nucleic acid molecule to a target cell, whereby the nucleic acid molecule transfected the cell and was expressed. In many studies, successful delivery and expression of a heterologous gene was achieved in preferred cell types and/or using preferred delivery vehicles and routes of administration of the present invention.

For example, using liposome delivery, U.S. Pat. No. 5,705,151, issued Jan. 6, 1998, to Dow et al. demonstrated the successful in vivo intravenous delivery of a nucleic acid molecule encoding a superantigen and a nucleic acid molecule encoding a cytokine in a cationic liposome delivery vehicle, whereby the encoded proteins were expressed in tissues of the animal, and particularly in pulmonary tissues. In addition, Liu et al., *Nature Biotechnology* 15:167, 1997, demonstrated that intravenous delivery of cholesterol-containing cationic liposomes containing genes preferentially targets pulmonary tissues and effectively mediates transfer and expression of the genes in vivo. Several publications by Dzau and collaborators demonstrate the successful in vivo delivery and expression of a gene into cells of the heart, including cardiac myocytes and fibroblasts and vascular smooth muscle cells using both naked DNA and Hemagglutinating virus of Japan-liposome delivery, administered by both incubation within the pericardium and infusion into a coronary artery (intracoronary delivery) (See, for example, Aoki et al., 1997, *J. Mol. Cell. Cardiol.* 29:949-959; Kaneda et al., 1997, *Ann N.Y. Acad. Sci.* 811:299-308; and von der Leyen et al., 1995, *Proc Natl Acad Sci USA* 92:1137-1141).

Delivery of numerous nucleic acid sequences has been accomplished by administration of viral vectors encoding the nucleic acid sequences. Using such vectors, successful delivery and expression has been achieved using ex vivo delivery (See, of many examples, retroviral vector; Blaese et al., 1995, *Science* 270:475-480; Bordignon et al., 1995, *Science* 270:470-475), nasal administration (CFTR-adenovirus-associated vector), intracoronary administration (adenoviral vector and Hemagglutinating virus of Japan, see above), intravenous administration (adeno-associated viral vector; Koeberl et al., 1997, *Proc Natl Acad Sci USA* 94:1426-1431). A publication by Maurice et al. (1999, *J. Clin. Invest.* 104:21-29) demonstrated that an adenoviral vector encoding a β2-adrenergic receptor, administered by intracoronary delivery, resulted in diffuse multichamber myocardial expression of the gene in vivo, and subsequent significant increases in hemodynamic function and other improved physiological parameters. Levine et al. describe in vitro, ex vivo and in vivo delivery and expression of a gene to human adipocytes and rabbit adipocytes using an adenoviral vector and direct injection of the constructs into adipose tissue (Levine et al., 1998, *J. Nutr. Sci. Vitaminol.* 44:569-572).

In the area of neuronal gene delivery, multiple successful in vivo gene transfers have been reported. Millecamps et al. reported the targeting of adenoviral vectors to neurons using neuron restrictive enhancer elements placed upstream of the promoter for the transgene (phosphoglycerate promoter). Such vectors were administered to mice and rats intramuscularly and intracerebrally, respectively, resulting in successful neuronal-specific transfection and expression of the transgene in vivo (Millecamps et al., 1999, *Nat. Biotechnol.* 17:865-869). As discussed above, Bennett et al. reported the use of adeno-associated viral vector to deliver and express a gene by subretinal injection in the neural retina in vivo for greater than 1 year (Bennett, 1999, ibid.).

Gene delivery to synovial lining cells and articular joints has had similar successes. Oligino and colleagues report the use of a herpes simplex viral vector which is deficient for the immediate early genes, ICP4, 22 and 27, to deliver and express two different receptors in synovial lining cells in vivo (Oligino et al., 1999, *Gene Ther.* 6:1713-1720). The herpes vectors were administered by intraarticular injection. Kuboki et al. used adenoviral vector-mediated gene transfer and intraarticular injection to successfully and specifically express a gene in the temporomandibular joints of guinea pigs in vivo (Kuboki et al., 1999, *Arch. Oral. Biol.* 44:701-709). Apparailly and colleagues systemically administered adenoviral vectors encoding IL-10 to mice and demonstrated successful expression of the gene product and profound therapeutic effects in the treatment of experimentally induced arthritis (Apparailly et al., 1998, *J. Immunol.* 160:5213-5220). In another study, murine leukemia virus-based retroviral vector was used to deliver (by intraarticular injection) and express a human growth hormone gene both ex vivo and in vivo (Ghivizzani et al., 1997, *Gene Ther.* 4:977-982). This study showed that expression by in vivo gene transfer was at least equivalent to that of the ex vivo gene transfer. As discussed above, Sawchuk et al. has reported successful in vivo adenoviral vector delivery of a gene by intraarticular injection, and prolonged expression of the gene in the synovium by pretreatment of the joint with anti-T cell receptor monoclonal antibody (Sawchuk et al., 1996, ibid. Finally, it is noted that ex vivo gene transfer of human interleukin-1 receptor antagonist using a retrovirus has produced high level intraarticular expression and therapeutic efficacy in treatment of arthritis, and is now entering FDA approved human gene therapy trials (Evans and Robbins, 1996, *Curr. Opin. Rheumatol.* 8:230-234). Therefore, the state of the art in gene therapy has led the FDA to consider human gene therapy an appropriate strategy for the treatment of at least arthritis. Taken together, all of the above studies in gene therapy indicate that delivery and expression of a recombinant nucleic acid molecule according to the present invention is feasible.

Another method of delivery of recombinant molecules is in a non-targeting carrier (e.g., as "naked" DNA molecules, such as is taught, for example in Wolff et al., 1990, *Science* 247, 1465-1468). Such recombinant nucleic acid molecules are typically injected by direct or intramuscular administration. Recombinant nucleic acid molecules to be administered by naked DNA administration include an isolated nucleic acid molecule of the present invention, and preferably includes a recombinant molecule of the present invention that preferably is replication, or otherwise amplification, competent. A naked nucleic acid reagent of the present invention can comprise one or more nucleic acid molecules of the present invention including a dicistronic recombinant molecule. Naked nucleic acid delivery can include intramuscular, subcutaneous, intradermal, transdermal, intranasal and oral routes of administration, with direct injection into the target tissue being most preferred. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun."

In the method of the present invention, therapeutic compositions can be administered to any member of the Vertebrate class, Mammalia, including, without limitation, primates, rodents, livestock and domestic pets. Preferred patients to protect are humans.

In accordance with the present invention, a suitable single dose size of a compound or composition is a dose that is capable of regulating the desired biological activity, when administered one or more times over a suitable time period. Doses can vary depending upon the goal of the administration or the condition or the disease being treated. Preferably, a protein or antibody of the present invention is administered in an amount that is between about 50 U/kg and about 15,000 U/kg body weight of the patient. In another embodiment, a protein or antibody is administered in an amount that is between about 0.01 µg and about 10 mg per kg body weight of the patient, and more preferably, between about 0.1 µg and about 100 µg per kg body weight of the patient. When the compound to be delivered is a nucleic acid molecule, an appropriate single dose results in at least about 1 pg of protein expressed per mg of total tissue protein per µg of nucleic acid delivered. More preferably, an appropriate single dose is a dose which results in at least about 10 pg of protein expressed per mg of total tissue protein per µg of nucleic acid delivered; and even more preferably, at least about 50 pg of protein expressed per mg of total tissue protein per µg of nucleic acid delivered; and most preferably, at least about 100 pg of protein expressed per mg of total tissue protein per µg of nucleic acid delivered. A preferred single dose of a naked nucleic acid vaccine ranges from about 1 nanogram (ng) to about 100 µg, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 µm in diameter) and are propelled into skin cells or muscle with a "gene gun." It will be obvious to one of skill in the art that the number of doses administered to a patient is dependent upon the goal of the administration (e.g., the extent of the disease or condition to be treated and the response of an individual patient to the treatment).

As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment) to reduce the symptoms of the disease. In particular, protecting a patient from a disease or enhancing another therapy (e.g., transplantation) is accomplished by regulating a given activity such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

More specifically, a composition of the present invention comprising CystC, a homologue or mimetic thereof, or other related compound, when administered to an animal by the method of the present invention, preferably produces a result which can include alleviation of the disease (e.g., reduction of at least one symptom or clinical manifestation of the disease), elimination of the disease, reduction of a tumor or lesion associated with the disease, elimination of a tumor or lesion associated with the disease, prevention or alleviation of a secondary disease resulting from the occurrence of a primary disease (e.g., metastatic cancer resulting from a primary cancer), prevention of the disease, and stimulation of effector cell immunity against the disease. In particular, the compositions of the present invention are effective to regulate TGF-β and/or cathepsin B activity and thereby regulate the downstream effects of such activities, and more particularly, to improve the therapeutic response to human malignancies, as well as a variety of proliferative and fibrotic diseases regulated by TGF-β.

Cancers to be treated or prevented using the methods and compositions of the present invention include, but are not limited to, melanomas, squamous cell carcinoma, breast cancers, head and neck carcinomas, thyroid carcinomas, soft tissue sarcomas, bone sarcomas, testicular cancers, prostatic cancers, ovarian cancers, bladder cancers, skin cancers, brain cancers, angiosarcomas, hemangiosarcomas, mast cell tumors, primary hepatic cancers, lung cancers, pancreatic cancers, gastrointestinal cancers, renal cell carcinomas, hematopoietic neoplasias, and metastatic cancers thereof. A therapeutic composition of the present invention is useful for inhibiting tumor malignancy by inhibiting (i) cathepsin B-mediated invasion, (ii) cathepsin B-mediated TGF-β activation, and/or (iii) TGF-β signal transduction. Preferably, the use of CystC and related compounds according to the present invention in an animal that has or is at risk of developing cancer produces a result selected from the group of alleviation of the cancer, prevention of metastatic cancer, or prevention of the primary cancer. In one embodiment, the use of CystC and related compounds is particularly desirable for the treatment of metastatic cancer or cancer that is later stage cancer.

Proliferative or fibrotic conditions or diseases mediated at least in part by TGF-β expression or activity that can be treated or prevented using the methods and compositions of the present invention include, but are not limited to, fibrosis (kidney, liver, pulmonary, etc.), excessive wound healing or scarring, hypertension, and organ transplant rejection (i.e., high TGF-β levels have been associated with rejection).

Certain diseases and conditions have been associated with increased levels of CystC and such diseases and candidates may also be treated by regulating the activity of CystC as described herein. Such diseases, include, but are not limited to, neurodegenerative diseases, rheumatoid arthritis and conditions associated with persistent pain.

One embodiment of the present invention relates to a method to identify a regulatory compound that regulates TGF-β activity, and preferably, that is an antagonist of TGF-β. Most preferably, the compound has the ability to inhibit the TGF-β stimulation of initiating metastatic events, including decreased cell polarization, reduced cell-cell contact, and elevated cell invasion and migration. The compound may also have the ability to regulate cathepsin B activity (e.g., a homologue of CystC), but such activity is not required of the compound of the present invention.

In one aspect of this embodiment, the method includes the steps of: (a) designing or identifying a putative antagonist compound based on the structure of Cystatin C (e.g., the primary or tertiary structure); (b) synthesizing the compound; and (c) selecting compounds from (b) that inhibit the biological activity of TGF-β. The Cystatin C can include Cystatin C from any animal species, but is preferably human Cystatin C. In this embodiment, the structure of Cystatin C can include the linear or primary structure, as well as the tertiary structure. Human Cystatin C has been crystallized and the structure determined, and the atomic coordinates for the tertiary structure of Cystatin C is found in the Protein Database Accession No. 1G96 (described in and deposited by Janowski et al., *Nat. Struct. Biol.* 8(4):316-320, 2001), incorporated herein by reference in its entirety. The following publications, each of which is incorporated herein by reference in its entirety, also describe the structure of CystC or cystatins: Ekiel et al., *J. Mol. Biol.* 271(2):266-277, 1997; Bode et al., *EMBO J.* 7(8): 2593-2599, 1988; and Kozak et al., *Acta Crystallog. D Biol. Crystallog.* 55(11):1939-1942, 1999. The primary or linear sequence of CystC from various animal species have been disclosed and described above, including various information regarding the structure-to-function relationship of the linear sequence.

Having the atomic coordinates that define the tertiary structure of the CystC protein, one can produce a representation or model of the three dimensional structure of a CystC protein, such as a computer model. A computer model of the present invention can be produced using any suitable software program, including, but not limited to, MOLSCRIPT 2.0 (Avatar Software AB, Heleneborgsgatan 21C, SE-11731 Stockholm, Sweden), the graphical display program O (Jones et. al., Acta Crystallography, vol. A47, p. 110, 1991), the graphical display program GRASP, or the graphical display program INSIGHT. Suitable computer hardware useful for producing an image of the present invention are known to those of skill in the art (e.g., a Silicon Graphics Workstation).

As used herein, the term "model" refers to a representation in a tangible medium of the three dimensional structure of a protein, polypeptide or peptide. For example, a model can be a representation of the three dimensional structure in an electronic file, on a computer screen, on a piece of paper (i.e., on a two dimensional medium), and/or as a ball-and-stick figure. Physical three-dimensional models are tangible and include, but are not limited to, stick models and space-filling models. One can image a model, for example, on a computer screen by expressing (or representing) and manipulating the model on a computer screen using appropriate computer hardware and software technology known to those skilled in the art (e.g., Evans and Sutherland, Salt Lake City, Utah, and Biosym Technologies, San Diego, Calif.). Computer screen images and pictures of the model can be visualized in a number of formats including space-filling representations, α carbon traces, ribbon diagrams and electron density maps.

A representation or model of the three dimensional structure of a CystC protein can also be determined using techniques which include molecular replacement or SIR/MIR (single/multiple isomorphous replacement). Methods of molecular replacement are generally known by those of skill in the art (generally described in Brunger, Meth. Enzym., vol. 276, pp. 558-580, 1997; Navaza and Saludjian, Meth. Enzym., vol. 276, pp. 581-594, 1997; Tong and Rossmann, Meth. Enzym., vol. 276, pp. 594-611, 1997; and Bentley, Meth. Enzym., vol. 276, pp. 611-619, 1997, each of which are incorporated by this reference herein in their entirety) and are performed in a software program including, for example, AmoRe (CCP4, Acta Cryst. D50, 760-763 (1994) or XPLOR. Briefly, X-ray diffraction data is collected from the crystal of a crystallized target structure. The X-ray diffraction data is transformed to calculate a Patterson function. The Patterson function of the crystallized target structure is compared with a Patterson function calculated from a known structure (referred to herein as a search structure). The Patterson function of the crystallized target structure is rotated on the search structure Patterson function to determine the correct orientation of the crystallized target structure in the crystal. The translation function is then calculated to determine the location of the target structure with respect to the crystal axes. Once the crystallized target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulfide bonds, and β-strands or β-sheets) of the search molecule are related to the crystallized target structure.

The model of the tertiary structure of the CystC protein can then be used to design or identify candidate compounds that are antagonists of TGF-β, for example, of that are predicted to have other CystC biological activity (e.g., cysteine protease inhibitory activity). Such compounds can be designed using structure based drug design, which refers to the prediction of a conformation of a peptide, polypeptide, protein, or conformational interaction between a peptide or polypeptide, and a compound, using the three dimensional structure of the peptide, polypeptide or protein. Typically, structure based drug design is performed with a computer. For example, generally, for a protein to effectively interact with (e.g., bind to) a compound, it is necessary that the three dimensional structure of the compound assume a compatible conformation that allows the compound to bind to the protein in such a manner that a desired result is obtained upon binding. Knowledge of the three dimensional structure of the protein enables a skilled artisan to design a compound having such compatible conformation, or to select such a compound from available libraries of compounds.

The step of designing compounds can include creating a new chemical compound or searching databases of libraries of known compounds (e.g., a compound listed in a computational screening database containing three dimensional structures of known compounds). Designing can also be performed by simulating chemical compounds having substitute moieties at certain structural features. The step of designing can include selecting a chemical compound based on a known function of the compound. A preferred step of designing comprises computational screening of one or more databases of compounds in which the three dimensional structure of the compound is known and is interacted (e.g., docked, aligned, matched, interfaced) with the three dimensional structure of a TGF-β receptor, for example, by computer (e.g. as described by Humblet and Dunbar, Animal Reports in Medicinal Chemistry, vol. 28, pp. 275-283, 1993, M Venuti, ed., Academic Press). Methods to synthesize suitable chemical compounds are known to those of skill in the art and depend upon the structure of the chemical being synthesized. Methods to evaluate the bioactivity of the synthesized compound depend upon the bioactivity of the compound (e.g., inhibitory or stimulatory) are described herein.

One embodiment of the present invention for structure based drug design comprises identifying a chemical compound that complements the shape of a CystC protein or a portion thereof (e.g., the portion that interacts with TGF-β receptors). Such method is referred to herein as a "geometric approach". In a geometric approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule, such as a ligand).

The geometric approach is described by Kuntz et al., J. Mol. Biol., vol. 161, p. 269, 1982, which is incorporated by this reference herein in its entirety. The algorithm for chemical compound design can be implemented using the software program DOCK Package, Version 1.0 (available from the Regents of the University of California). Pursuant to the Kuntz algorithm, the shape of the cavity or groove on the surface of a structure at a binding site or interface is defined as a series of overlapping spheres of different radii. One or more extant databases of crystallographic data (e.g., the Cambridge Structural Database System maintained by University Chemical Laboratory, Cambridge University, Lensfield Road, Cambridge CB2 1EW, U.K.) or the Protein Data Bank maintained by Brookhaven National Laboratory, is then searched for chemical compounds that approximate the shape thus defined.

Chemical compounds identified by the geometric approach can be modified to satisfy criteria associated with chemical complementarity, such as hydrogen bonding, ionic interactions or Van der Waals interactions.

Preferably, a compound that is identified by the method of the present invention originates from a compound having chemical and/or stereochemical complementarity with CystC or a portion thereof. Such complementarity is characteristic of a compound that matches the structure of the protein either in shape or in distribution of chemical groups and binds to TGF-β receptor (e.g., TβRII) to inhibit TGF-β binding and/or inhibit cellular signal transduction in a cell expressing the TGF-β receptor. More preferably, a compound that binds to a ligand binding site of the TGF-β receptor associates with an affinity of at least about $10^{-6}$ M, and more preferably with an affinity of at least about $10^{-7}$M, and more preferably with an affinity of at least about $10^{-8}$ M.

The compounds of the present invention can be synthesized from readily available starting materials. Various substituents on the compounds of the present invention can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups are known in the art, and can be employed. Examples of many of the possible groups can be found in "Protective Groups in Organic Synthesis" by T. W. Green, John Wiley and Sons, 1981, which is incorporated herein in its entirety. For example, nitro groups can be added by nitration and the nitro group can be converted to other groups, such as amino by reduction, and halogen by diazotization of the amino group and replacement of the diazo group with halogen. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono-and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product, including isolated products.

Since the compounds of the present invention can have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to one of ordinary skill in the art. This would further be dependent upon the ring involved.

It is to be understood that the scope of this invention encompasses not only the various isomers which may exist but also the various mixtures of isomers which may be formed.

If the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety results in forms that are separable by fractional crystallization, distillation or chromatography.

When the compounds of the present invention contain an olefin moiety and such olefin moiety can be either cis- or trans-configuration, the compounds can be synthesized to produce cis- or trans-olefin, selectively, as the predominant products. Alternatively, the compound containing an olefin moiety can be produced as a mixture of cis- and trans-olefins and separated using known procedures, for example, by chromatography as described in W. K. Chan, et al., J. Am. Chem. Soc., 1974, 96, 3642, which is incorporated herein in its entirety.

In the final step of the method, compounds identified by the structure-based design or identification can be evaluated for bioactivity, and particularly, the ability to regulate TGF-β activity, and most particularly, to antagonize the activity of TGF-β, using any of the methods described herein (above and below) and further include any art known method of evaluating TGF-β activity. Such methods include, but are not limited to, detection of the ability of the compound to bind to TGF-β receptor, and particularly to TβRII, or detection of the ability of the compound to inhibit TGF-β-responsive gene expression, or the ability of the compound to inhibit TGF-β-mediated tumor cell malignancy and invasion.

In another aspect of this embodiment, the method of identifying compounds includes the steps of: (a) identifying proteins that are structural homologues of Cystatin C; and (b) evaluating proteins from (a) that are capable of regulating the biological activity of TGF-β. For example, the ability of the protein of (a) to bind to a receptor for TGF-β, such as TβRII can be evaluated. Methods of producing and identifying compounds that are structural homologues of CystC using computer design and the geometric approach, for example, have been described in detail above. Given the structural information provided herein and especially the structure-to-function information correlating CystC with its biological activities, one of skill in the art will also be able to produce more simple protein homologues, including fragments, of CystC for use in these methods. Methods for producing protein homologues of CystC have been described in detail above, and can simply be identified and designed by sequence analysis and selection of appropriate modifications that can be introduced using conventional molecular techniques (e.g., recombinant production of a homologue or fragment).

In yet another aspect of this embodiment, the method includes the steps of: (a) contacting a cell that expresses a TGF-β receptor and Cystatin C with a putative regulatory compound; (b) detecting the expression of Cystatin C in the cell; and (c) comparing the expression of Cystatin C after contact with the compound to the expression of Cystatin C before contact with the compound, wherein detection of a change in the expression of Cystatin C in the cells after contact with the compound as compared to before contact with the compound indicates that the compound is a putative regulator of TGF-β and TGF-β signal transduction. Alternatively, one can contact a cell that expresses a TGF-β receptor with TGF-β and a putative homologue or mimetic of CystC and determine whether the putative homologue or mimetic of CystC regulates the activation of the TGF-β receptor by TGF-β. Other variations and combinations of TGF-β, its receptors, CystC and homologues thereof can be used in similar assays to determine the ability of candidate regulatory compounds to regulate TGF-β activity in a manner commensurate with the regulation of TGF-β activity by wild-type CystC. Putative regulatory compounds can be added to the assay system prior to, simultaneously with, or after the addition or provision of other compounds in the assay (e.g., cells, TGF-β, CystC, etc.). The above-described assays may also be performed using non-cell based assays, where the ability of a regulatory compound to mimic the biological activity of wild-type CystC and/or to specifically regulate TGF-β-mediated activities in a CystC-specific manner are evaluated (e.g., by contacting TGF-β and/or its receptor, or CystC and a TGF-β receptor, with a putative regulatory compound and evaluating binding or another activity).

As used herein, the term "putative" or "candidate" refers to compounds having an unknown regulatory activity, at least with respect to the ability of such compounds to regulate expression of a gene or protein or the biological activity of a protein as described herein. In the method of identifying a regulatory compound according to the present invention, the method can be a cell-based assay, or non-cell based assay. In accordance with the present invention, a cell-based assay is conducted under conditions which are effective to screen for regulatory compounds useful in the method of the present invention. Effective conditions include, but are not limited to, appropriate media, temperature, pH and oxygen conditions that permit cell growth.

In one embodiment, the conditions under which a protein according to the present invention is contacted with a putative regulatory compound, such as by mixing, are conditions in which the protein is not stimulated (activated) if essentially no regulatory compound is present.

In an alternate embodiment, the conditions under which a protein according to the present invention is contacted with a putative regulatory compound, such as by mixing, are conditions in which the protein is normally stimulated (activated) if essentially no regulatory compound is present.

The present methods involve contacting cells with the compound being tested for a sufficient time to allow for interaction, activation or inhibition of the protein by the compound. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring.

The assay of the present invention can also be a non-cell based assay. In this embodiment, the putative regulatory compound can be directly contacted with an isolated protein, or a protein component (e.g., an isolated extracellular portion of a receptor, or soluble receptor), and the ability of the putative regulatory compound to bind to the protein or protein component can be evaluated, such as by an immunoassay or other binding assay. The assay can then include the step of further analyzing whether putative regulatory compounds which bind to a portion of the protein are capable of increasing or decreasing the activity of the protein. Such further steps can be performed by cell-based assay, as described above, or by non-cell-based assay.

Methods to evaluate any compounds identified by any of the above-described methods for use in any of the methods of the invention have been discussed in detail elsewhere herein. Agonists and antagonists identified by the above methods or any other suitable method are useful in a variety of therapeutic methods as described herein.

The following experimental results are provided for purposes of illustration and are not intended to limit the scope of the invention.

EXAMPLES

The following Materials and Methods were used in Examples 1-7 below.
Human Cystatin C Plasmids
A retroviral CystC vector was synthesized by PCR amplifying the full-length human CystC cDNA from EST 4183311. The resulting PCR product was shuttled through the pcDNA3.1/Myc-His B vector (InVitrogen) at Eco RI (N-terminus) and Xho I (C-terminus) restriction sites to C-terminally tag human CystC with Myc- and (His)6-tags. Afterward, the resulting tagged CystC cDNA was PCR amplified using oligonucleotides containing Eco RI (N-terminus) and Xho I (C-terminus) restriction sites, and subsequently ligated into identical sites immediately upstream of the IRES in the bicistronic retroviral vector, pMSCV-IRES-GFP (42).

Synthesis of a retroviral Δ14CystC vector proceeded by PCR amplifying the pGEX-4T1-contained Δ14CystC cDNA insert (see below), which was shuttled through the pSecTag B vector (InVitrogen) at Nco I (N-terminus) and Bgl II (C-terminus) restriction sites. This cloning step C-terminally tagged the Δ14CystC cDNA with the Myc- and (His)6-tags, as well as appended the Ig leader sequence to its N-terminus to permit its secretion when expressed in mammalian cells. The resulting tagged Δ14CystC was PCR amplified using oligonucleotides containing Hpa I (N-terminus) and Eco RI (C-terminus) restriction sites that facilitated ligation of the PCR fragment into pMSCV-IRES-GFP. When expressed in mammalian cells, Δ14CystC protein was slightly larger than that of its corresponding wild-type CystC due to additional N-terminal amino acids appended to Δ14CystC by the pSec-Tag vector.

All CystC and Δ14CystC cDNA inserts were sequenced in their entirety on an Applied Biosystems 377A DNA sequencing machine.

Fusion Protein Construction and Purification

A CystC fusion protein was synthesized by PCR amplifying full-length human CystC cDNA (less its signal sequence) using oligonucleotides containing Eco RI (N-terminus) and Xho I (C-terminus) restriction sites. The resulting PCR fragment was subcloned into the C-terminus of glutathione S-transferase encoded by the bacterial expression vector, pGEX-4T1 (Amersham Pharmacia Biotech). Site-directed mutagenesis of GST-CystC to delete its conserved cysteine proteinase inhibitor motif (Δ14CystC; residues 80-93) was performed using the QuikChange site-directed mutagenesis kit (Stratagene) according to the manufacturer's recommendations. All fusion cDNA inserts were sequenced in their entirety on an Applied Biosystems 377A DNA sequencing machine.

The expression and purification of various GST fusion proteins from transformed *E. coli* was as described previously (43).

Soluble TβR-II Plasmid

A soluble human TGF-β type II receptor (TβR-II) was synthesized by PCR amplifying the extracellular domain of TβR-II (sTβR-II; nucleotides 72-516) using oligonucleotides containing Kpn I (N-terminus) and Not I (C-terminus) restriction sites. The resulting PCR product was ligated into corresponding sites in the pSecTag B vector, which C-terminally tagged the sTIβR-II cDNA with Myc- and (His)6-tags and appended the Ig leader sequence at its N-terminus. The resulting sTβR-II was sequenced in its entirety on an Applied Biosystems 377A DNA sequencing machine.

Isolation and Identification of Murine CystC

Murine 3T3-L1 fibroblasts were cultured in 15-cm plates in Dulbecco's modified Eagle's medium (DMEM) supplemented with 10% fetal bovine serum until attaining 90% confluency. The cells were then rendered quiescent by extensive washing in PBS, followed by incubation in serum-free DMEM for 12 hr at 37° C. Quiescent 3T3-L1 cells were metabolically labeled with [35S]methionine in the absence or presence of TGF-β1 (10 ng/ml) for 12 hr at 37° C. Afterward, naive- and TGF-β-conditioned media were collected (10 plates/condition), clarified by centrifugation, and concentrated initially to ~3 ml in an Amicon concentrator (1000 Da MWC) and ultimately via by trichloroacetic acid/deoxycholate precipitation. The resulting protein pellets were resuspended, neutralized, and precipitated with acetone prior to their resuspension in isoelectric focusing buffer (8M urea, 4% CHAPS, 10 mM DTT, and 0.2% 3-10 ampholytes). Protein samples were applied to 11 cm pH 3-10 isoelectric focusing strips and developed according to the manufacturer's recommendations (3 strips/condition; Amersham Pharmacia Biotech). The isoelectric focused proteins were then fractionated through 10% SDS-PAGE, and subsequently transferred electrophoretically to Immobilon-P (Millipore). Secreted proteins were visualized by Coomassie staining and autoradiography of the dried membranes. A differentially expressed ~18 kDa protein that was evident in TGF-β-conditioned media was excised from the membranes and sequenced using the Sequelon-AA sequencing kit (ABI).

Northern Blotting

Quiescent 3T3-L1 cells were incubated in the absence or presence of TGF-β1 (5 ng/mL) for 0-48 hr, and subsequently were harvested in RNAzol Reagent (Tel-Test) to isolate total RNA. Ten μg of total RNA was then electrophoresed through 1.2% agarose/formaldehyde gels and transferred to nylon membrane. The immobilized RNA was probed with a 32P-labeled human CystC cDNA probe for 1 hr at 68° C. in ExpressHyb (Clontech). Afterward, the membrane was washed according to the manufacturer's instructions, and Cystatin C mRNA was visualized by autoradiography.

Tumor Array

The effects of tumorigenesis on CystC expression were examined by hybridizing a 32P-radiolabeled full-length human CystC cDNA probe to a matched human normal/tumor cDNA array according to the manufacturer's instructions (Clontech). CystC expression in normal and malignant human tissues was visualized by autoradiography. cDNA array was stripped and reprobed with a 32P-labeled ubiquitin cDNA probe provided by the manufacturer. The expression of CystC was normalized to that of ubiquitin, and the ratio of CystC expression between individual pairs of normal and tumor tissue was determined. A ratio of $\geq 2$ or $\leq 0.5$ was considered significant.

Retroviral Infections

Control (i.e., pMSCV-IRES-GFP), CystC, or Δ14CystC retroviral supernatants were produced by EcoPac2 retroviral packaging cells (Clontech) and used to infect murine 3T3-L1 fibroblasts and human HT1080 fibrosarcoma cells as described previously (42). Forty-eight hr post-infection, the highest 10% of GFP-expressing cells were collected on a MoFlo cell sorter(Cytomation), and subsequently expanded to yield stable populations of control, CystC-, or Δ14CystC-expressing cells having equivalent GFP levels at a positivity rate of >90%.

Western Blotting

Conditioned media (2 ml) of 3T3-L1 cells stably expressing GFP, CystC or Δ14Cyst C were collected, clarified by centrifugation, and concentrated by trichloroacetic acid/deoxycholate precipitation. The proteins were fractionated through 12% SDS-PAGE gel and subsequently transferred electrophoretically to nitrocellulose. The membrane was probed with anti-CystC polyclonal antibodies (1:1000, Upstate Biotechnology), and the resulting immunocomplexes were visualized by enhanced chemiluminescence.

Invasion Assays

The effect CystC and D14CystC on the invasion of HT1080 and 3T3-L1 cells was determined as described previously (42). Briefly, upper chambers were coated with 100 μl of diluted Matrigel (1:50 in serum-free media), which was allowed to evaporate to dryness overnight at room temperature. The following morning the Matrigel mixtures were rehydrated and subsequently cultured with control-, CystC-, or D14CystC-expressing HT1080 or 3T3-L1 cells at a density of 100,000 cells/chamber. Cellular invasion was stimulated by addition of 2% serum to the lower chambers. Forty-eight hr later, the cells were washed twice in ice-cold PBS and immediately fixed for 15 min with 95% ethanol. Cells remaining in the upper chambers were removed with a cotton swab, whereas those remaining in the lower chamber were stained with crystal violet. Quantifying invading cells was determined through two independent measures, which yielded identical results: (i) manual counting under a light microscope, and (ii) crystal violet dye extraction by incubation of the membranes in 10% acetic acid, followed by spectrophotometry at 590 nm.

In some experiments, the effects of recombinant CystC and D14CystC on 3T3-L1 cell invasion was examined. To do so, 3T3-L1 cells (100,000 cells/chamber) were allowed to invade through Matrigel in the absence or presence of 10 mg/ml of recombinant GST, GST-CystC, or D14CystC, together with or without 5 ng/ml of TGF-β1. All subsequent procedures were performed as described above.

Luciferase Reporter Gene Assays

Analysis of luciferase activity driven by the synthetic p3TP reporter ((26); generously provided by Dr. Joan Massague, Sloan Kettering) was performed as described previously (42). Briefly, control, CystC-, or Δ14CystC-expressing 3T3-L1 or HT1080 cells were cultured onto 24-well plates at a density of 45,000 cells/well and allowed to adhere overnight. The cells were transiently transfected the following morning by overnight exposure to LT1 liposomes (Mirus) containing 300 ng/well p3TP-luciferase and 100 ng/well of pCMV-β-gal. Afterward, the cells were washed twice with PBS and stimulated overnight in serum-free media with increasing concentrations of TGF-β1 as indicated. The following morning, luciferase and β-gal activities contained in detergent-solubilized cell extracts were determined.

In some experiments, the effects of recombinant CystC and D14CystC on p3TP-luciferase activity 3T3-L1 cells was determined. To do so, 3T3-L1 cells were transiently transfected as above, and subsequently stimulated with TGF-β1 (5 ng/ml) in the absence or presence of 10 mg/ml of recombinant GST, GST-CystC, or D14CystC. All subsequent procedures were performed as described above.

Iodinated TGF-β1 Radioligand Binding and Cross-Linking Assay

Mink lung Mv1Lu epithelial cells were plated onto 6-well plates and grown until 90% confluency. The radioligand binding and cross-linking of iodinated TGF-β1 (200 pM) to Mv1Lu cells in the absence or presence of increasing concentration of recombinant GST-Jun(1-79) or -CystC was performed as described previously (44). Afterward, cytokine:receptor complexes contained in detergent-solubilized whole cell extracts were isolated by immunoprecipitation with anti-TβR-II antibodies as described previously (44). TGF-β1 bound to cell surface TβR-I, TβR-II, and TβR-III was visualized by exposure of the dried gels to a phosphor screen, which were developed 1-3 d later on a Molecular Dynamic Typhoon Scanner. Total bound TGF-β1 was defined as the sum of signal intensities for TGF-β1 cross-linked to TβR-I, TβR-II, and TβR-III in each condition.

In Vitro TGF-β1 Binding Assay

Human kidney 293T cells were plated onto 6-well plates and allowed to adhere overnight. The cells were transiently transfected the following morning by overnight exposure to LT1 liposomes containing 1 μg/well sTβR-II, which encodes for the extracellular domain of TβR-II that is Myc-His-tagged at its C-terminus, and subsequently were placed in serum-free DMEM for an additional 24 hr. Afterward, the conditioned-media were collected and cleared of cellular debris by a microcentrifugation. The resulting clarified supernatants were supplemented with [$^{125}$I]TGF-β1, together with or without recombinant CystC (10 μg/ml), and subsequently were tumbled for 2 hr at 4° C. Afterward, TGF-β1:sTβR-II complexes were isolated by immunoprecipitation with monoclonal anti-Myc antibodies (1 μg/mL; Covance) and fractionated through 12% SDS-PAGE. TGF-β1 bound to recombinant sTβR-II was visualized by a 1-3 d exposure of the dried gels to a phosphor screen, which subsequently was developed on a Molecular Dynamic Typhoon Scanner.

Example 1

The following example demonstrates that TGF-β1 induces CystC expression in 3T3-L1 cells.

TGF-β governs cell microenvironments by regulating fibroblast expression and secretion of cytokines, growth factors, and ECM proteins that alter the survival, proliferation, and motility of normal and cancer cells. To identify fibroblast secretory proteins whose expression are regulated by TGF-β, the inventor collected, concentrated, and fractionated by 2D-electrophoresis proteins present in naive- and TGF-β-conditioned media of murine 3T3-L1 fibroblasts. Fractionated proteins were immobilized to Immobilon-P, and were visualized by Coomassie staining and autoradiography. Differentially expressed proteins regulated by TGF-β were excised and subjected to Edman sequencing. The results showed that a highly basic protein of ~18 kDa was prominently induced by TGF-β (data not shown). Edman sequencing of this protein returned an amino acid sequence of (NH2)-ATPKQGPR-(COOH) (positions 21-28 of SEQ ID NO:4), corresponding to residues 21-28 of murine CystC.

TGF-β previously has been shown to stimulate CystC transcript expression in murine embryo cells (18). To confirm that CystC expression was indeed induced by TGF-β and to establish the mechanism for this effect, northern blot analysis was performed on total RNA isolated from TGF-β-treated 3T3-L1 cells. TGF-β stimulated 3T3-L1 cells to synthesize CystC transcript in a time-dependent manner (data not shown). Collectively, these findings establish CystC as a novel gene target for TGF-β in 3T3-L1 cells, ultimately leading to increased production and secretion of CystC protein.

Example 2

The following example shows that tumorigenesis alters CystC expression in human tissues.

Altered CystC expression has been associated with the development of human pathologies, particularly cancer (3). In order to identify human cancers potentially susceptible to altered CystC expression, a radiolabeled human CystC cDNA probe was hybridized to a membrane arrayed with matched normal/tumor cDNAs generated from cancer patients (data not shown). CystC expression was normalized to that of ubiquitin and normal:tumor tissue CystC expression rations were determined. Ratios $\geq 2$ or $\leq 0.5$ were considered significant. Of the 68 patients surveyed, CystC expression was altered in 65% (44/68) of the tumors, of which 84% (37/44) showed downregulation. Significantly attenuated CystC expression was especially evident in cancers of the stomach (100%; 8/8 cases), prostate (100%; 3/3 cases), uterus (71%; 5/7 cases), kidney (60%; 9/15 cases), rectum (57%; 4/7 cases), and colon (55%; 6/11 cases). More importantly, CystC expression was aberrant in 69% of metastatic human malignancies (15/25), of which 73% (11/15) showed downregulated CystC expression. Taken together, these findings support the notion that CystC normally functions to suppress tumor formation, as well as the processes of invasion and metastasis.

Example 3

The following example demonstrates that CystC inhibits cathepsin B-mediated invasion in HT1080 cells.

Cathepsin B is a lysosomal cysteine proteinase that functions in intracellular protein catabolism, as well as in bone resorption, hormone activation, and antigen processing (5). During tumorigenesis, cancer cells express a cathepsin B splice variant whose protein product is secreted into the extracellular milieu (5) and localized to the leading edge of invasive tumors (19), thereby promoting cancer cell invasion and metastasis. However, recent evidence has questioned the role of intracellular versus extracellular cathepsin B in promoting cancer cell invasion (20). To distinguish between these two possibilities, human HT1080 fibrosarcoma cells that stably express the murine ecotropic receptor (21) were infected with control (i.e., GFP), CystC, or Δ14CystC retrovirus. Afterward, cells that expressed GFP were isolated by flow cytometry to establish stable polyclonal populations of control-, CystC-, and Δ14CystC-expressing HT1080 cells (data not shown). The inventor chose to study HT1080 cells because they are highly invasive, and because they express large quantities of secreted cathepsin B and comparably little CystC (22). Thus, if extracellular cathepsin B mediates HT1080 cell invasion, it was hypothesized that overexpression of secreted CystC would attenuate their invasion through synthetic basement membranes.

Briefly, GFP-, CystC-, or Δ14CystC-expressing HT0180 cells were allowed to invade through Matrigel-coated membranes for 48 hr. Data shown in FIG. 1A are the mean (±SE) of three (Δ14CystC) and nine (GFP and CystC) independent experiments presented as the percent invasion relative to GFP-expressing HT1080 cells (***, $p<0.05$; Student's T-Test).

Accordingly, CystC expression significantly inhibited HT1080 cell invasion through Matrigel matrices (FIG. 1A). In contrast, expression of Δ14CystC, which lacks the cysteine inhibitor motif and thus is unable to inactivate cathepsin B (23), failed to affect HT1080 cell invasion (FIG. 1A). Furthermore, treating HT1080 cells with the cell impermeable cathepsin B inhibitor II (Calbiochem) significantly reduced their invasion through Matrigel matrices (by 47.1±8.5%; n=3, $p<0.05$), while treatment with the cell permeable cathepsin B inhibitor, CA-074ME (Calbiochem), failed to effect their invasiveness (101.0±5.6% of control; n=3).

Taken together, these findings indicate that HT1080 cell invasion occurs in part through the proteinase activities of extracellular, not lysosomal, cathepsin B. These findings also suggest that measures designed to augment CystC concentrations within tumor microenvironments will negate the oncogenic effects of cathepsin B.

Example 4

The following example shows that CystC inhibits TGF-β-responsive reporter gene expression via a cathepsin B-independent mechanism in HT1080 cells.

During tumorigenesis, TGF-β is frequently converted from a suppressor to a promoter of cancer cell growth, invasion, and metastasis (17, 24). Stimulation of HT1080 cells with TGF-β had no effect on their invasion through Matrigel matrices, nor on their expression of CystC (data not shown). Thus, while TGF-β clearly regulates CystC expression in murine embryo (18) and 3T3-L1 (Example 1) cells, the coupling of TGF-β to CystC expression in HT1080 cells appears dysregulated. CystC has also been reported to stimulate DNA synthesis in normal and transformed murine Swiss 3T3 fibroblasts (10), and in rat mesangial cells (11), as well as inhibit melanoma cell motility (25). However, overexpression of CystC or Δ14CystC in HT1080 cells failed to effect their synthesis of DNA and migration to fibronectin (data not shown).

Extracellular cathepsin B expression has been linked to the activation of latent TGF-β from inactive ECM depots (6, 7). The inventor therefore hypothesized that CystC expression might impact TGF-β signaling via a cathepsin B-dependent mechanism. To test this hypothesis, changes in luciferase expression driven by the synthetic p3TP-luciferase reporter gene (26) were measured in control- and CystC-expressing HT1080 cells. Briefly, GFP-, CystC-, or Δ14CystC-expressing HT0180 cells were transiently transfected with p3TP-luciferase and pCMV-β-gal. The transfectants were stimulated with increasing concentrations of TGF-β1 (0-5 ng/ml) as indicated, and subsequently processed to measure luciferase and β-gal activities. Data are the mean (±SE) luciferase activities of four independent experiments normalized to untreated GFP-expressing cells.

Figure 1B:
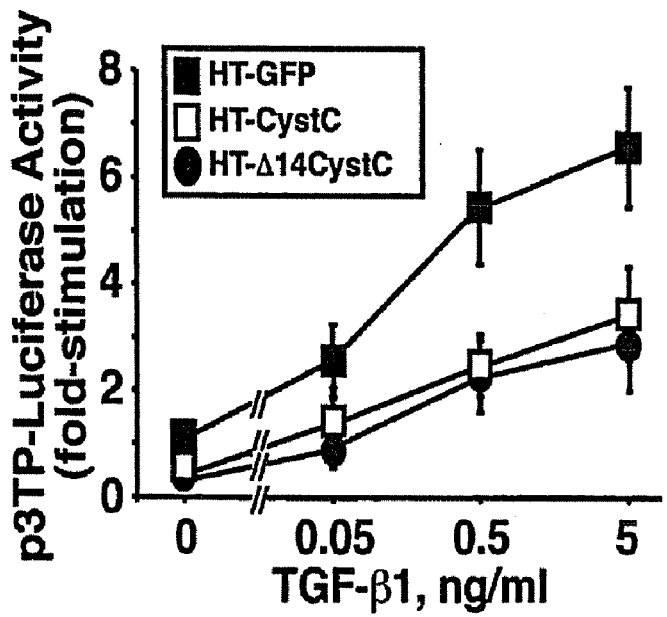
FIG. 1B is a line graph showing that expression of Δ14CystC, which lacks the cysteine inhibitor motif and thus is unable to inactivate cathepsin B, failed to affect HT1080 cell invasion.

As shown in FIG. 1B, CystC significantly inhibited TGF-β-stimulated luciferase activity driven by the p3TP promoter. Surprisingly, Δ14CystC was equally effective as CystC in inhibiting luciferase activity stimulated by TGF-β (FIG. 1B). Collectively, these findings identify CystC as a novel antagonist of TGF-β signaling, doing so through a cathepsin B-independent pathway.

Example 5

The following example shows that CystC inhibits tonic and TGF-β-stimulated invasion in 3T3-L1 cells.

CystC previously has been reported to regulate cell proliferation (10, 11) and motility (25). Similar to HT1080 cells, the inventor found that CystC failed to effect 3T3-L1 cell DNA synthesis and migration to fibronectin (data not shown). However, the inventor has found that 3T3-L1 fibroblasts readily invade through Matrigel matrices, and that TGF-β enhances their ability to do so (see below). To determine the effects of CystC on the invasiveness of 3T3-L1 cells, stable polyclonal populations of 3T3-L1 cells expressing GFP, CystC, or Δ14CystC were generated by bicistronic retroviral infection. Briefly, murine 3T3-L1 cells were infected with ecotropic retrovirus encoding either GFP (i.e., control), CystC, or D14CystC. The infectants were FACS-sorted by GFP expression (highest 10%) to yield stable polyclonal populations of control, CystC, and D14CystC-expressing 3T3-L1 cells having equivalent GFP expression levels at a positivity rate of ≧90%. Immunoblotting 3T3-L1 cell conditioned-media with anti-CystC antibodies demonstrated that 3T3-L1 cells transduced with CystC- or D14CystC-retroviruses constitutively secrete recombinant CystC proteins into the medium. The resulting 3T3-L1 cell lines had purities 90% and expressed GFP indistinguishably (data not shown). Furthermore, 3T3-L1 cells infected with CystC or Δ14CystC retroviruses expressed and secreted high levels of recombinant CystC protein into the media, while those infected with control retrovirus (i.e., GFP) were negative for recombinant CystC expression (data not shown).

Figure 2A:
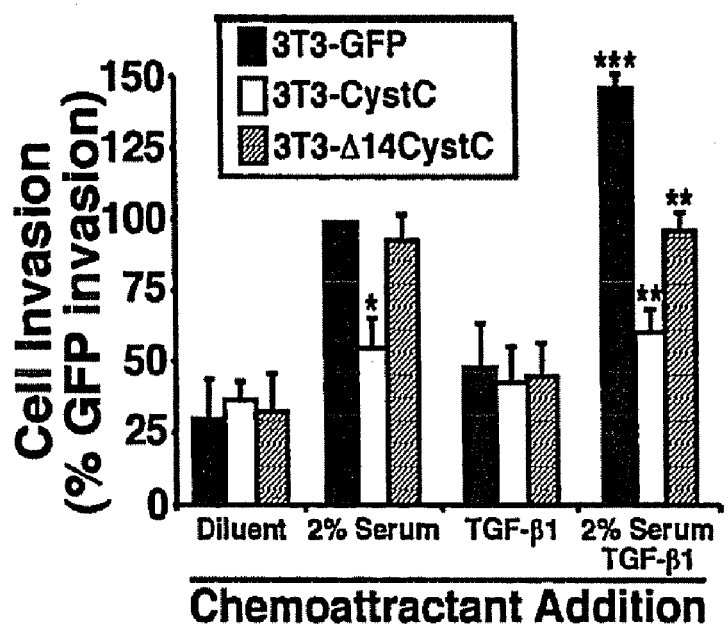
FIG. 2A is a bar graph showing that 3T3-L1 cells that readily invaded through Matrigel matrices when stimulated by serum are unaffected by Δ14CystC, but are inhibited significantly by CystC.

GFP-, CystC-, or Δ14CystC-expressing 3T3-L1 cells were allowed to invade through Matrigel-coated filters in the absence or presence of TGF-β1 (5 ng/ml) for 48 hr, and the results are shown in FIG. 2A. As expected, 3T3-L1 cells readily invaded through Matrigel matrices when stimulated by serum: this response was unaffected by Δ14CystC, but was inhibited significantly by CystC (FIG. 2A). FIG. 2A also shows that 3T3-L1 cells treated with TGF-β exhibited a trend towards enhanced invasion; however, TGF-β treatment in combination with serum induced significantly more 3T3-L1 cell invasion than that by serum alone (FIG. 2A). Interestingly, CystC expression blocked both components of 3T3-L1 cell invasion, whereas Δ14CystC blocked only the TGF-β-dependent component (FIG. 2A). Data are the mean (±SE) of four independent experiments presented as the percent invasion relative to GFP-expressing 3T3-L1 cells. TGF-β1 significantly enhanced 3T3-L1 cell invasion (***, $p<0.05$; Student's T-Test). CystC expression significantly inhibited tonic (*, $p<0.05$; Student's T-Test) and TGF-β1-stimulated (, $p<0.05$; Student's T-Test) 3T3-L1 cell invasion, while Δ14CystC expression only significantly inhibited TGF-β-stimulated 3T3-L1 cell invasion (, $p<0.05$; Student's T-Test).

Figure 2B:
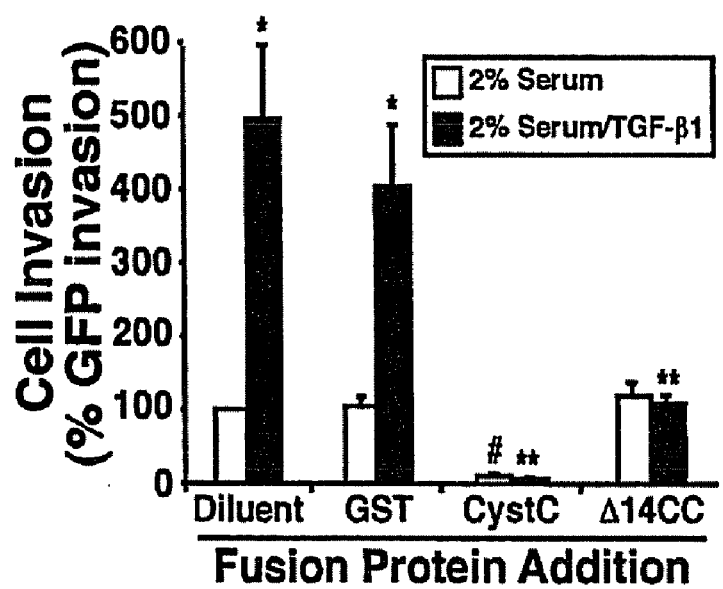
FIG. 2B is a bar graph showing that recombinant CystC administration blocked 3T3-L1 cell invasion stimulated by serum and serum:TGF-β, whereas recombinant Δ14CystC selectively blocked that by TGF-β.

Moreover, the inhibitory effects of CystC on 3T3-L1 cell invasion could be recapitulated by addition of recombinant CystC fusion proteins. Control or TGF-β1-stimulated (5 ng/ml) 3T3-L1 cells were allowed to invade through Matrigel-coated filters for 48 hr in the absence or presence of recombinant (10 mg/ml) GST, GST-CystC, or GST-D14CystC as indicated in FIG. 2B. As shown in FIG. 2B, treatment of 3T3-L1 cells with recombinant GST (10 mg/ml) failed to effect their invasion induced by serum or serum: TGF-β. In contrast, recombinant CystC administration blocked 3T3-L1 cell invasion stimulated by serum and serum: TGF-β, whereas recombinant Δ14CystC selectively blocked that by TGF-β (FIG. 2B). Data are the mean (±SE) of three independent experiments presented as the percent invasion relative to untreated 3T3-L1 cells. TGF-β1 significantly enhanced 3T3-L1 cell invasion (*, $p<0.05$; Student's T-Test). Recombinant CystC significantly inhibited tonic (#, $p<0.05$; Student's T-Test) and TGF-β1-stimulated (, $p<0.05$; Student's T-Test) 3T3-L1 cell invasion, while Δ14CystC expression only significantly inhibited TGF-β-stimulated 3T3-L1 cell invasion (, $p<0.05$; Student's T-Test). Collectively, these findings indicate that 3T3-L1 cell invasion proceeds through cathepsin B-dependent and TGF-β-dependent pathways. Moreover, the present inventor's findings show that CystC abrogated both pathways, while Δ14CystC blocked only the TGF-β-stimulated pathway.

Example 6

The following example demonstrates that CystC and ΔCystC inhibit TGF-β-stimulated reporter gene expression in 3T3-L1 cells.

Figure 3A:
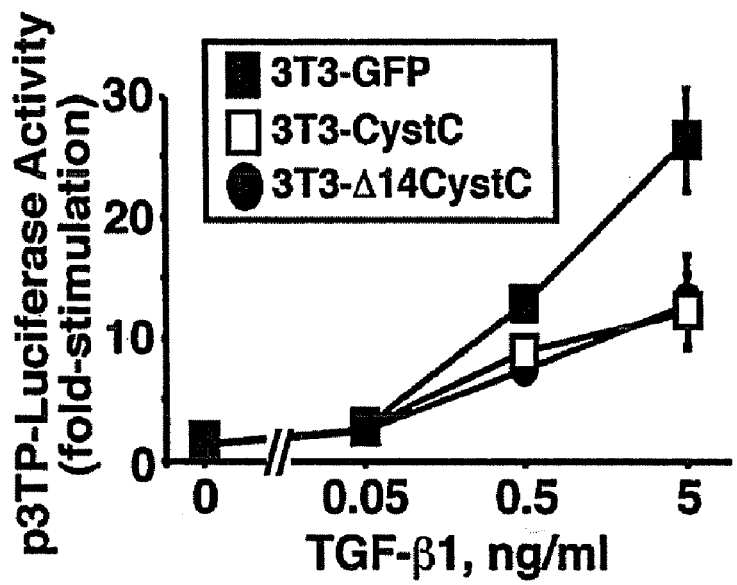
FIG. 3A is a line graph showing that expression of either CystC or Δ14CystC significantly reduced TGF-β-stimulated luciferase activity as compared to control cells.

The present inventor's findings that TGF-β signaling was inhibited by CystC (FIGS. 1 and 2) independent of its actions on cathepsin B lead them to hypothesize CystC as a general antagonist of TGF-β signaling. To test this hypothesis, changes in p3TP-driven luciferase activity were monitored in control, CystC-, Δ14CystC-expressing cells before and after their stimulation with TGF-β. Briefly, GFP-, CystC-, or Δ14CystC-expressing 3T3-L1 cells were transiently transfected with p3TP-luciferase and pCMV-β-gal, and subsequently stimulated with increasing concentrations of TGF-β1 (0-5 ng/ml) as indicated in FIG. 3A. Afterward, luciferase and β-gal activities contained in detergent-solubilized cell extracts were measured. FIG. 3A shows that expression of either CystC or Δ14CystC significantly reduced TGF-β-stimulated luciferase activity as compared to control cells. Data are the mean (±SE) luciferase activities of four independent experiments normalized to untreated GFP-expressing cells.

Figure 3B:
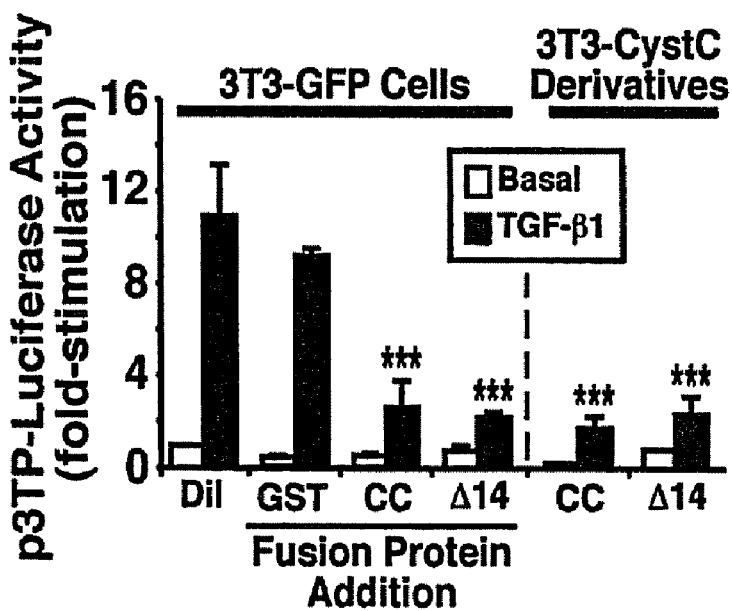
FIG. 3B is a bar graph showing that recombinant CystC and Δ14CystC both significantly inhibited luciferase activity stimulated by TGF-β in 3T3-L1 cells.

The transfectants were then stimulated with TGF-β1 (5 ng/ml) in the absence or presence of recombinant (10 mg/ml) GST, GST-CystC, or GST-D14CystC as indicated in FIG. 3B. Similar to their effects on 3T3-L1 cell invasion, recombinant CystC and Δ14CystC both significantly inhibited luciferase activity stimulated by TGF-β in 3T3-L1 cells (FIG. 3B). Data are the mean (±SE) luciferase activities of five independent experiments normalized to untreated GFP-expressing cells. CystC and Δ14CystC significantly inhibited TGF-β-stimulated luciferase activity driven by the synthetic p3TP promoter (***, $p<0.05$; Student's T-Test).

Taken together, these findings identify CystC as a novel antagonist of TGF-β signaling, doing so through a cathepsin B-independent mechanism.

Example 7

The following example shows that CystC antagonizes TGF-β1 binding to TGF-β receptors.

The present inventor's findings thus far have identified CystC as a novel TGF-β antagonist (FIGS. 1-3). The ability of recombinant CystC (and Δ14CystC) to recapitulate the inhibitory effects of CystC expression on TGF-β signaling lead the inventor to speculate that CystC inhibits TGF-β signaling by antagonizing the interaction between TGF-β and its receptors. This hypothesis seemed especially attractive given the fact that the Type 3 cystatin family member, fetuin (also known as α2-HS-glycoprotein), inhibits TGF-β signaling by physically interacting with and preventing the binding of TGF-β to its receptors (27-29).

Figure 4A:
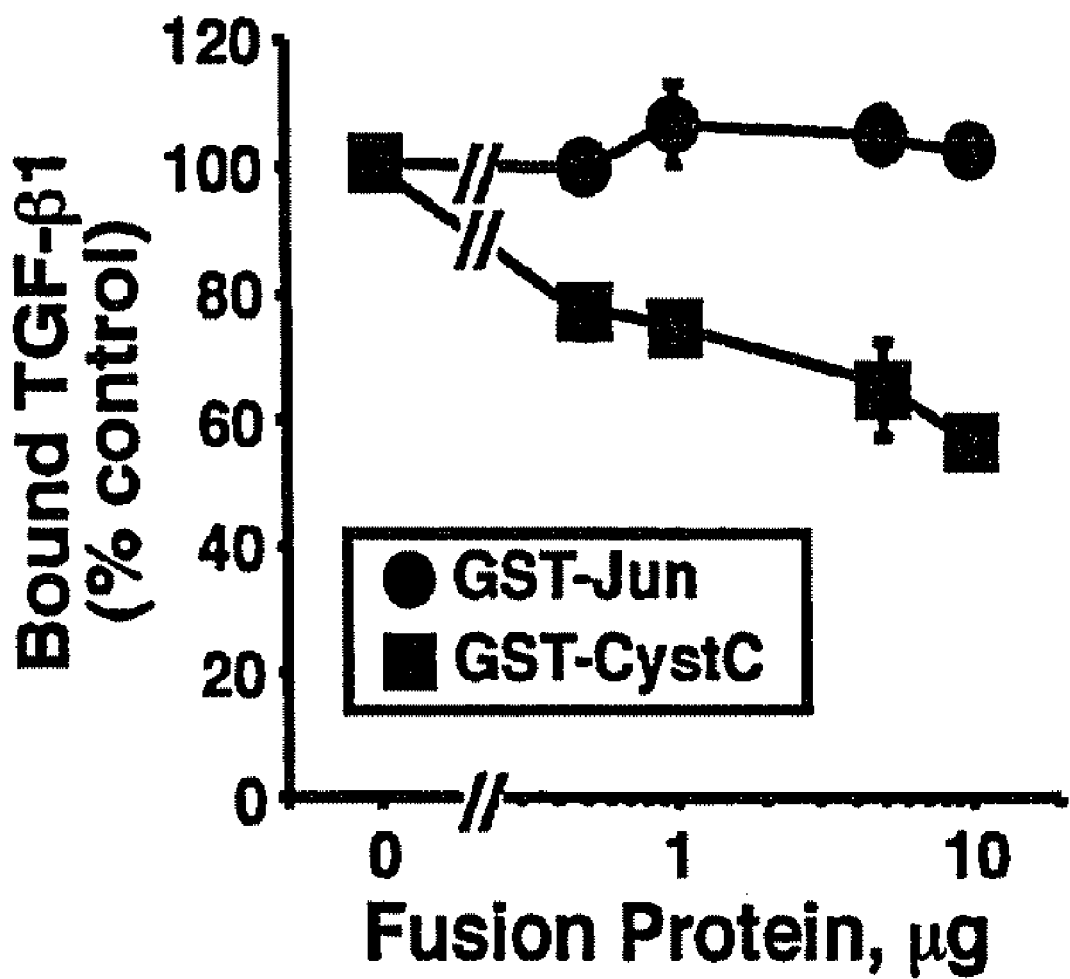
FIG. 4A is a line graph showing CystC that antagonizes TGF-β1 binding to TGF-β receptors.

Mink lung Mv1Lu epithelial cells were incubated for 3 hr at 4° C. with [125I]TGF-β1 (200 pM) in the absence or presence of increasing concentrations (0-10 μg/ml; 0, 0.5, 1, 5, 10) of recombinant Jun(1-79) or CystC. Cytokine:receptor complexes were cross-linked by addition of disuccinimidyl suberate, and subsequently isolated from detergent-solubilized whole cell extracts by immunoprecipitation with anti-TβR-II antibodies. Although co-immunoprecipitation and affinity pull-down assays both failed to demonstrate a direct physical interaction between CystC and TGF-β1 (data not shown), iodinated TGF-β1 binding and cross-linking assays showed that recombinant CystC dose-dependently inhibited the binding of TGF-β to its cell surface receptors (FIG. 4A). The reduction in TGF-β1 binding was specific to CystC because increasing concentrations of recombinant Jun(1-79) had no effect on the binding of iodinated TGF-β1 to its receptors (FIG. 4A). Data were generated based on a representative phosphor image of iodinated TGF-β1 bound to TβR-I, TβR-II, and TβR-III. FIG. 4A depicts the mean TGF-β1 (±SE) binding observed in six independent experiments and is presented as the percent TGF-β1 binding normalized to that in the absence of added fusion protein. This finding implicates CystC as a novel TGF-β receptor antagonist.

Figure 4B:
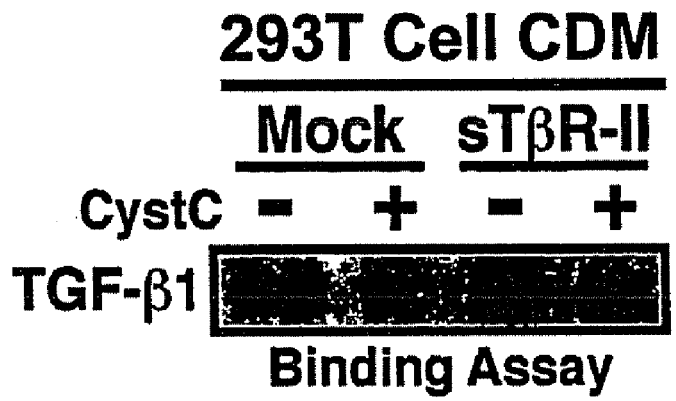
FIG. 4B is a graph showing that CystC inhibits TGF-β binding to TβR-II.
Figure 4B:
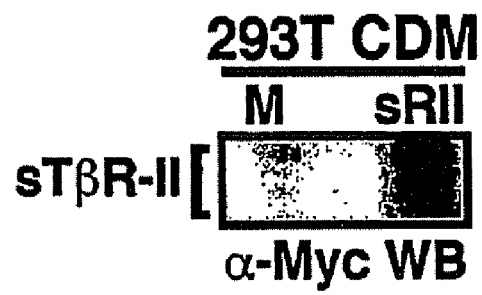
Figure 4B:
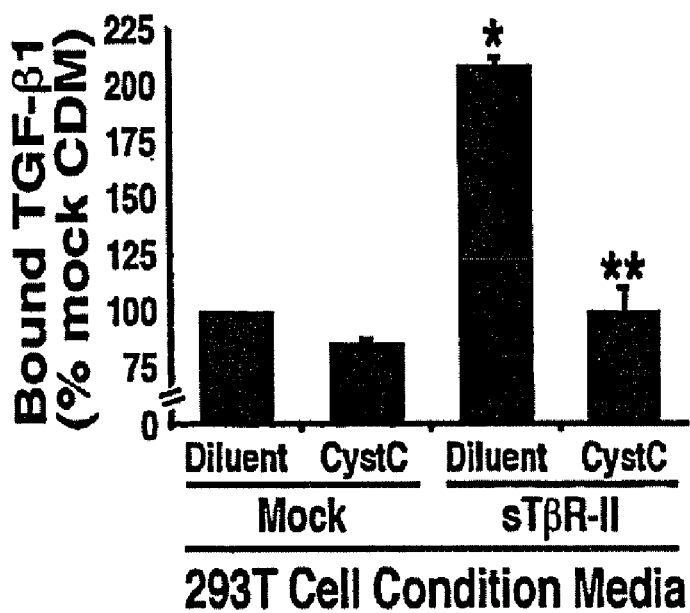

Transmembrane signaling by TGF-β commences by its binding to either TβR-III, which then associates with and binds to TβR-II, or directly to TβR-II, which then associates with and binds to the TβR-I (17, 30). The experiment above demonstrated that CystC equally reduced the binding of TGF-β1 to all three of its cell surface receptors, which suggests that CystC selectively antagonized initial TGF-β binding, not its subsequent receptor multimerization. The inventor therefore hypothesized that CystC antagonized TGF-β binding to TβR-II. To test this hypothesis, an in vitro TGF-β capture assay was performed that measured the effects of CystC on the binding of iodinated TGF-β1 to soluble human TβR-II. This TβR-II construct was chosen for study because it binds TGF-β (31) and has itself been used to antagonize TGF-β signaling (32-34). Briefly, human 293T cells were transiently transfected with the ligand binding extracellular domain of TβR-II (sTβR-II), which is a soluble, secreted protein. Conditioned-media from mock- or sTβR-II-transfected 293T cells was collected and incubated for 2 hr at 4° C. with [125I]TGF-β1 (200 pM) in the absence or presence of recombinant CystC (10 μg/ml). Cytokine:receptor complexes were isolated by immunoprecipitation with anti-Myc antibodies. As expected, significantly more iodinated TGF-β1 was captured by conditioned media containing sTβR-II than was captured by control media (FIG. 4B). More importantly, recombinant CystC completely abrogated the binding of iodinated TGF-β1 to sTβR-II (FIG. 4B). Upper panel shows a representative autoradiograph of iodinated TGF-β1 bound to sTβR-II, while lower panel depicts the mean TGF-β1 (±SE) binding from three independent experiments presented as the percent TGF-β1 binding normalized to conditioned-media of mock transfected cells without added fusion protein. sTβR-II significantly enhanced TGF-β1 capture from conditioned-media (*, p<0.05; Student's T-Test). The binding of TGF-β1 to sTβR-II was significantly reduced by recombinant CystC (**, p<0.05; Student's T-Test).

Collectively, these findings have identified CystC as a novel antagonist of TGF-β signaling, doing so by inhibiting TGF-β binding to TβR-II.

The following Materials and Methods were used in Examples 8-9 below.

Recombinant CystC Expression and Purification

The synthesis of bacterial expression vectors encoding human CystC or Δ14CystC fused to the C-terminus of GST, as well as their purification from transformed *E. coli* was described in Examples 1-7 above.

Retroviral CystC Expression

The creation of bicistronic retroviral vectors (i.e., pMSCV-IRES-GFP) encoding human CystC or Δ14CystC were described previously in Examples 1-7 above. Mouse NMuMG MECs and rat NRK kidney fibroblasts were infected overnight with control (i.e., pMSCV-IRES-GFP), CystC, or Δ14CystC retroviral supernatants produced by EcoPac2 retroviral packaging cells (Clontech) as described above. Cells expressing GFP were isolated and collected 48 h later on a MoFlo cell sorter (Cytomation), and subsequently were expanded to yield stable polyclonal populations of control-, CystC, or Δ14CystC-expressing cells. The expression and secretion of recombinant CystC proteins by infected NMuMG and NRK cells was monitored by immunoblotting conditioned-media with anti-CystC antibodies as described above.

Immunofluorescence Studies

The ability of TGF-β to alter actin cytoskeletal architecture and E-cadherin expression was monitored essentially as described (Piek et al., 1999). Briefly, control-, CystC-, or Δ14CystC-expressing NMuMG cells were allowed to adhere overnight to glass coverslips in 24-well plates (50,000 cells/well). The cells were stimulated the following day with TGF-β1 (5 ng/ml) for 0-36 hours at 37° C. In some experiments, control NMuMG cells were stimulated with TGF-β1 in the absence or presence of 10 μg/ml of recombinant GST, GST-CystC, or GST-Δ14CystC. Upon completion of agonist stimulation, the cells were washed in ice-cold PBS and immediately fixed in 3.7% formaldehyde. After extensive washing in PBS, the cells were blocked in PBS supplemented with 1.5% FBS, followed by incubation with rhodamine-phalloidin (0.25 μM). Alternatively, the cells were blocked in goat γ-globulin (200 μg/ml; Jackson Immunoresearch) prior to visualizing E-cadherin by sequential incubations with monoclonal anti-E-cadherin (1:50 dilution; BD Bioscience), followed by biotinylated goat anti-mouse antibody (5 μg/ml; Jackson Immunoresearch), and finally by Alexa-streptavidin (1.2 μg/ml; Molecular Probes). Images were captured on a Nikon Diaphot microscope.

The ability of TGF-β to alter E-cadherin expression also was monitored by immunoprecipitating E-cadherin from Buffer H/1% Triton X-100-solubilized (Schiemann et al., 2003) NMuMG whole cell extracts, followed by immunoblotting with anti-E-cadherin antibodies (1:1000 dilution).

Soft Agar Assay

The growth of NRK cells in soft agar was performed according to the procedures described in (Moustakas et al., 1999). Briefly, duplicate cultures of control-, CystC-, or Δ14CystC-expressing NRK cells (10,000 cells/plate) were grown in 0.3% agar on a cushion of 0.6% agar in 35-mm plates. NRK cell growth in the absence or presence of TGF-β1 (5 ng/ml) was allowed to proceed for 7 d, whereupon the number of colonies formed was quantified under a light microscope.

Example 8

The following example demonstrates that CystC prevents TGF-β stimulation of EMT in NMuMG cells.

The importance of EMT in promoting cancer progression and tumor metastasis is becoming increasingly apparent (Thiery, 2002; Grunert, 2003). Although the formation and growth of early stage tumors is normally suppressed by TGF-β, cancer progression typically enables TGF-β to stimulate the growth and metastasis of late stage tumors, in part through its induction of EMT (Grunert, 2003). The inventor describes in Examples 1-7 above the cysteine protease inhibitor CystC as a novel TβR-II antagonist. Indeed, the physical association of CystC with TβR-II not only prevented TGF-β binding and, consequently, TGF-β signaling in normal and cancer cells, but also inhibited their invasion through synthetic basement membranes. Collectively, these findings led the inventor to hypothesize CystC as a novel chemopreventive agent capable of antagonizing TGF-β oncogenicity in late stage tumors, particularly the ability of TGF-β to induce EMT.

To test this hypothesis, the inventor first examined whether CystC and a CystC mutant impaired in its ability to inhibit cathepsin protease activity (i.e., Δ14CystC) could antagonize TGF-β stimulation of EMT in MECs. In contrast to developing tissues, inappropriate induction of EMT by TGF-β in adult tissues enhances tumorigenesis. TGF-β stimulation of EMT is studied routinely in murine NMuMG MECs, which readily undergo EMT when treated with TGF-β (Piek et al., 1999; Miettinen et al., 1994; Gotzmann et al., 2004). Briefly, NMuMG cells were stimulated with TGF-β1 (5 ng/ml) for 0-24 hours in the presence of 10 μg/ml of either GST, GST-CystC, or GST-Δ14CystC. Afterward, altered actin cytoskeletal architecture was visualized by direct rhodamine-phalloidin immunofluorescence. In a second experiment, NMuMG cells were stimulated with TGF-β1 (5 ng/ml) for 36 hours in the presence of GST fusion proteins as above. E-cadherin expression was monitored by indirect immunofluorescence with anti-E-cadherin antibodies. The results (data not shown) demonstrated that unstimulated NMuMG cells exhibited typical epithelial cuboidal morphology characterized by strong cortical and diffuse cytoplasmic actin staining In response to TGF-β, NMuMG cells transition into fibroblasts and exhibited distinct actin stress fibers emanating from focal adhesions.

In another experiment, NMuMG cells were infected with ecotropic retrovirus encoding either GFP (i.e., control), CystC, or Δ14CystC, and subsequently were isolated by FACS-sorting for GFP expression to yield stable polyclonal populations of control, CystC, and Δ14CystC-expressing cells. The expression and secretion of recombinant CystC proteins by infected NMuMG and NRK cells was monitored by immunoblotting conditioned-media with anti-CystC antibodies. The same cells were incubated in the absence or presence of TGF-β1 (5 ng/ml) for 8 hours, whereupon alterations in actin cytoskeletal architecture was visualized by direct rhodamine-phalloidin immunofluorescence. Next, the control, CystC-, and Δ14CystC-expressing NMuMG cells were incubated in the absence or presence of TGF-β1 (5 ng/ml) for 36 hours, whereupon E-cadherin expression was monitored by immunoblotting with anti-E-Cadherin antibodies. Finally, control, CystC-, and Δ14CystC-expressing NMuMG cells were allowed to invade through Matrigel matrices in the absence or presence of TGF-β1 (5 ng/ml) for 48 hours.

Figure 5A:
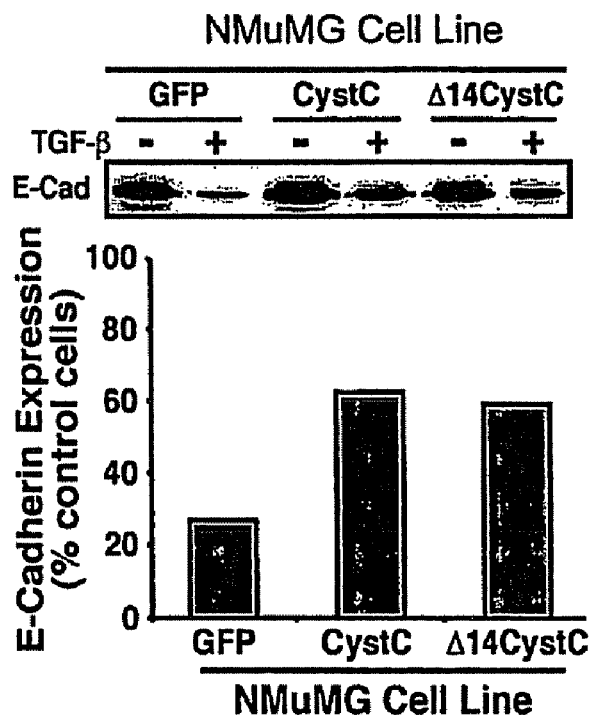
FIG. 5A is a bar graph showing that recombinant CystC or Δ14CystC treatment of or their overexpression in NMuMG cells prevented actin cytoskeletal reorganization stimulated by TGF-β, as well as antagonized TGF-β-mediated down-regulation of E-cadherin.
Figure 5B:
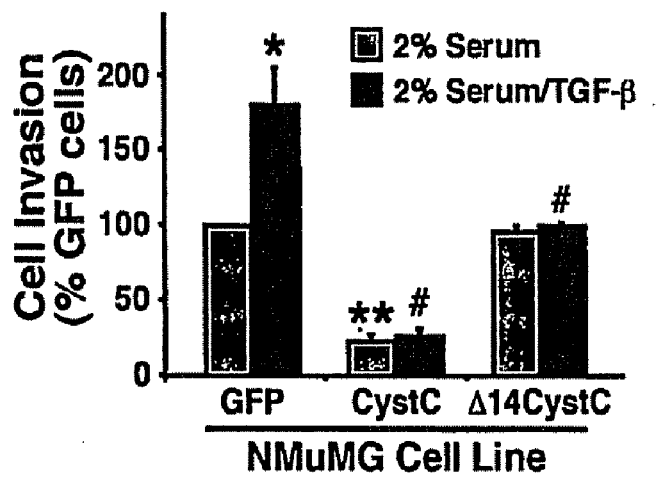
FIG. 5B is a bar graph showing that CystC and Δ14CystC expression inhibited and delineated cathepsin- and TGF-β-dependent invasion in NMuMG cells.

Recombinant CystC or Δ14CystC treatment of or their overexpression in NMuMG cells prevented actin cytoskeletal reorganization stimulated by TGF-β, as well as antagonized TGF-β-mediated downregulation of E-cadherin (FIG. 5A; values depict downregulation of E-cadherin expression induced by TGF-β relative to matched untreated NMuMG cells; this representative experiment was repeated twice with similar results). In addition, NMuMG cells undergoing EMT exhibit elevated invasion through synthetic basement membranes (FIG. 5B). Similar to their actions on 3T3-L1 cells, CystC and Δ14CystC expression also inhibited and delineated cathepsin- and TGF-β-dependent invasion in NMuMG cells (FIG. 5B). Values are the mean (±SE) of three independent experiments presented as the percent invasion relative to GFP-expressing NMuMG cells. TGF-β1 significantly enhanced NMuMG cell invasion (*, $p<0.05$; Student's t-Test), a response that was inhibited significantly by CystC and Δ14CystC expression (#, $p<0.05$; Student's t-Test). CystC expression also significantly inhibited tonic NMuMG cell invasion (*, $p<0.05$; Student's t-Test).

Collectively, these findings show that CystC and Δ14CystC do indeed effectively inhibit mammary cell EMT and invasion stimulated by TGF-β. Moreover, these findings suggest that future therapies employing CystC or Δ14CystC will prove effective in alleviating late stage tumor progression stimulated by TGF-β.

Example 9

The following example shows that CystC prevents TGF-β stimulation of morphological transformation in NRK cells.

The loss of cell polarity and the ability of cancer cells to grow autonomously in an anchorage-independent manner is a hallmark of cancer (Thiery, 2002; Grunert et al., 2003). TGF-β originally was described as a secreted factor that stimulates morphological transformation in rat NRK-49 kidney cells, leading to their acquisition of anchorage-independent growth in soft agar (Roberts et al., 1981; Assoian et al., 1983). Thus, in addition to promoting EMT, TGF-β also enhances cancer progression by stimulating morphological transformation and anchorage-independent cell growth. Because CystC and Δ14CystC both eliminated EMT stimulated by TGF-β, the present inventor hypothesized that these TβR-II antagonists would similarly inhibit NRK cell morphological transformation stimulated by TGF-β.

This hypothesis was tested by infecting NRK cells with bicistronic retrovirus encoding either CystC or Δ14CystC to determine their effects on NRK anchorage-independent growth stimulated by TGF-β. Briefly, rat NRK kidney fibroblasts were infected with control (i.e., pMSCV-IRES-GFP), CystC, or Δ14CystC retroviral supernatants, and the resulting infected cells were isolated by GFP fluorescence on a MoFlo cell sorter 48 hours later. Control, CystC-, and Δ14CystC-expressing NRK cells were cultured in soft-agar in the absence or presence of TGF-β1 (5 ng/ml) for 7 d, whereupon NRK colony formation was quantified by light microscopy. In addition, control, CystC-, and Δ14CystC-expressing NRK cells were allowed to invade through Matrigel matrices in the absence or presence of TGF-β1 (5 ng/ml) for 48 hours.

Figure 6A:
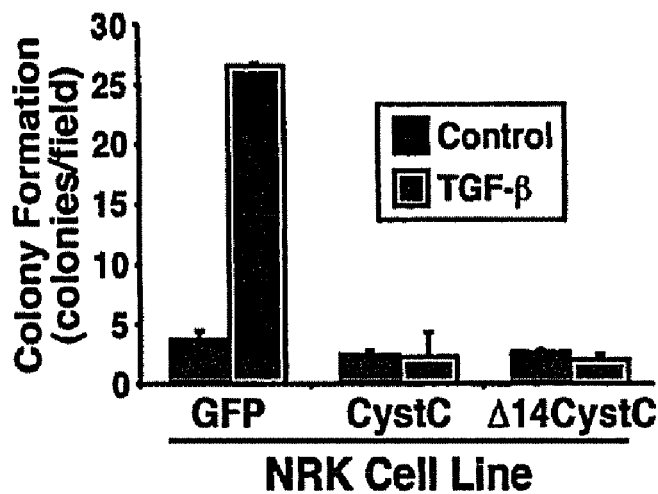
FIG. 6A is a bar graph showing that retroviral-mediated expression of CystC or Δ14CystC in NRK cells completely prevented morphological transformation stimulated by TGF-β.
Figure 6B:
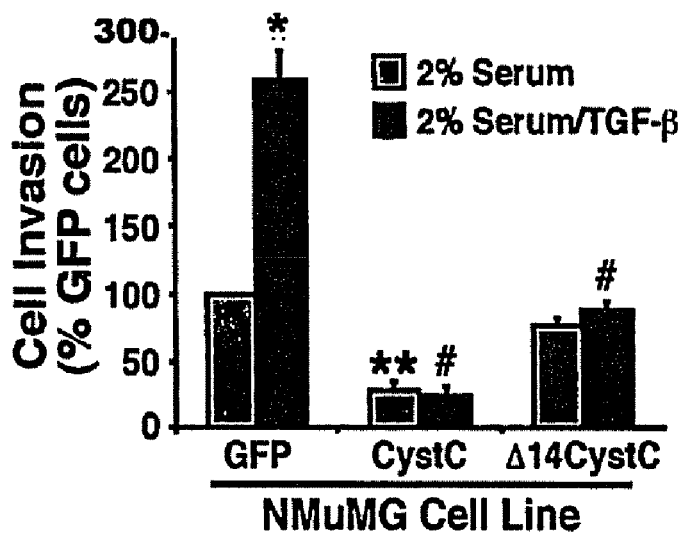
FIG. 6B is a bar graph showing that retroviral-mediated expression of CystC or Δ14CystC in NRK cells completely prevented TGF-β stimulation of NRK cell invasion through synthetic basement membranes.

As expected, TGF-β treatment enabled NRK cells to grow in an anchorage-independent manner when cultured in soft agar (FIG. 6A). Values are the mean (±SE) colony formation per microscope field observed in five independent experiments. Similar to their inhibitory activities in NMuMG cells, retroviral-mediated expression of CystC or Δ14CystC in NRK cells completely prevented morphological transformation stimulated by TGF-β (FIG. 6A), as well as TGF-β stimulation of NRK cell invasion through synthetic basement membranes (FIG. 6B). Values are the mean (±SE) of three independent experiments presented as the percent invasion relative to GFP-expressing NRK cells. TGF-β1 significantly enhanced NRK cell invasion (*, $p<0.05$; Student's t-Test). This TGF-β response was inhibited significantly by CystC and Δ14CystC expression (#, $p<0.05$; Student's t-Test), while tonic NRK cell invasion was only inhibited significantly by CystC expression (*, $p<0.05$; Student's t-Test).

Thus, in addition to preventing TGF-β stimulation of EMT, CystC and Δ14CystC also effectively inhibit morphological transformation and anchorage-independent growth stimulated by TGF-β.

REFERENCES

Each of the publications cited below and elsewhere herein is incorporated herein by reference in its entirety.

1. Vray et al., Cell. Mol. Life Sci., 59: 1503-1512, 2002.
2. Brown and Dziegielewska, Protein Sci., 6: 5-12, 1997.
3. Kos et al., Int. J. Biol. Markers, 15: 84-89, 2000.
4. Yan, S., Sameni, M., and Sloane, B. F., Biol. Chem., 379: 113-123, 1998.
5. Mort, J. S. and Buttle, D. J., Int. J. Biochem. Cell Biol., 29: 715-720, 1997.
6. Somanna et al., J. Biol. Chem., 277: 25305-25312, 2002.
7. Guo et al., J. Biol. Chem., 277: 14829-14837. 2002.
8. Nycander et al., FEBS Lett., 422: 61-64, 1998.
9. Bjork et al., Biochemistry, 35: 10720-10726, 1996.
10. Sun, Exp. Cell Res., 180: 150-160, 1989.
11. Tavera et al., Biochem. Biophys. Res. Commun., 182: 1082-1088, 1992.
12. Olafsson et al., Brain Pathol., 6: 121-126, 1996.
13. Schuck et al., Nephron. Clin. Pract., 93: c146-151, 2003.
14. Zore et al., Biol. Chem., 382: 805-810, 2001.
15. Kos et al., Clin. Chem., 44: 2556-2557, 1998.
16. De Vos et al., Oncogene, 21: 6848-6857, 2002.
17. Blobe et al., N. Engl. J. Med., 342: 1350-1358, 2000.
18. Solem et al., Biochem. Biophys. Res. Commun., 172: 945-951, 1990.
19. Calkins et al., J. Histochem. Cytochem., 46: 745-751. 1998.
20. Szpaderska and Frankfater, Cancer Res., 61: 3493-3500, 2001.
21. Hua et al., Genes Dev., 12: 3084-3095, 1998.
22. Corticchiato et al., Int. J. Cancer, 52: 645-652, 1992.

23. Auerswald et al., Eur. J. Biochem., 209: 837-845, 1992.
24. Massague et al., Cell, 103: 295-309, 2000.
25. Sexton and Cox, Melanoma Res., 7: 97-101, 1997.
26. Wrana et al., Cell, 71: 1003-1014, 1992.
27. Szweras et al., J. Biol. Chem., 277: 19991-19997, 2002.
28. Binkert et al., J. Biol. Chem., 274: 28514-28520, 1999.
29. Demetriou et al., J. Biol. Chem., 271: 12755-12761, 1996.
30. Massague, Nat. Rev. Mol. Cell Biol., 1: 169-178, 2000.
31. Lin et al., J. Biol. Chem., 270: 2747-2754, 1995.
32. Rowland-Goldsmith et al., Clin. Cancer Res., 7: 2931-2940, 2001.
33. Smith et al., Circ. Res., 84: 1212-1222, 1999.
34. Won et al., Cancer Res., 59: 1273-1277, 1999.
35. Liotta and Kohn, Nature, 411: 375-379, 2001.
36. Elenbaas and Weinberg, Exp. Cell Res., 264: 169-184. 2001.
37. Konduri et al., Oncogene, 21: 8705-8712, 2002.
38. Coulibaly et al., Int. J. Cancer, 83: 526-531. 1999.
39. Derynck et al., Nat. Genet., 29: 117-129. 2001.
40. Wakefield et al., J. Mammary Gland Biol. Neoplasia, 6: 67-82, 2001.
41. Huh et al., Mol. Pathol., 52: 332-340, 1999.
42. Schiemann et al., J. Biol. Chem., 277: 27367-27377, 2002.
43. Schiemann et al., Proc. Natl. Acad. Sci. USA, 92: 5361-5365, 1995.
44. Schiemann et al., Blood, 94: 2854-2861, 1999.
45. Thiery, Nat Rev Cancer 2002, 2:442-454.
46. Grunert et al., Nat Rev Mol Cell Biol 2003, 4:657-665.
47. Yoshida et al., J Natl Cancer Inst 2000, 92:1717-1730.
48. Fidler, Differentiation 2002, 70:498-505.
49. Siegel and Massague, Nat Rev Cancer 2003, 3:807-821.
50. Wakefield and Roberts, Curr Opin Genet Dev 2002, 12:22-29.
51. Cui et al., Cell 1996, 86:531-542.
52. Tang et al., J Clin Invest 2003, 112:1116-1124.
53. Sokol et al., Mol Cancer Res 2004, 2:183-195.
54. Piek et al., J Cell Sci 1999, 112:4557-4568.
55. Schiemann et al., Mol Biol Cell 2003, 14:3977-3988.
56. Moustakas et al., J Cell Sci 1999, 112:1169-1179.
57. Miettinen et al., J Cell Biol 1994, 127:2021-2036.
58. Gotzmann et al., Mutat Res 2004, 566:9-20.
59. Roberts et al., Proc Natl Acad Sci USA 1981, 78:5339-5343.
60. Assoian et al., J Biol Chem 1983, 258:7155-7160.
61. Oft et al., Curr Biol 1998, 8:1243-52.
62. Oft et al., Genes Dev 1996, 10:2462-2477.
63. Portella et al., Cell Growth Differ 1998, 9:393-404.
64. Oft et al., Nat Cell Biol 2002, 4:487-494.
65. Janda et al., J Cell Biol 2002, 156:299-313.
66. Bhowmick et al., Mol Biol Cell 2001, 12:27-36.
67. Bhowmick et al., J Biol Chem 2001, 276:46707-46713.
68. Bakin et al., J Biol Chem 2000, 275:36803-36810.
69. Yu et al., EMBO J 2002, 21:3749-3759.
70. Kowanetz et al., Mol Cell Biol 2004, 24:4241-4254.
71. Kang and Massague, Cell 2004, 118:277-279.
72. Huber et al., J Clin Invest 2004, 114:569-581.
73. Turk et al., Adv Enzyme Regul 2002, 42:285-303.
74. Turk Bet al., Biochim Biophys Acta 2000, 1477:98-111.
75. Roshy et al., Cancer Metastasis Rev 2003, 22:271-286.
76. Gantt et al., J Immunol 2003, 170:2613-2620.
77. Sinha et al., Prostate 1995, 26:171-178.
78. Sameni et al., Neoplasia 2000, 2:496-504.
79. Choong and Nadesapillai, Clin Orthop 2003, 415:S46-S58.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. An isolated Cystatin C homologue, wherein the amino acid sequence of the homologue differs from SEQ ID NO:2 by a deletion of amino acid residues from about position 80 to about position 93 with reference to SEQ ID NO:2, wherein the Cystatin C homologue inhibits TGF-β biological activity.

2. An isolated protein comprising a fragment of SEQ ID NO:2 that inhibits TGF-β biological activity, wherein the fragment differs from SEQ ID NO:2 by a deletion of at least 30 amino acids from the N-terminus of SEQ ID NO:2 and comprises at least the last 45 amino acids of SEQ ID NO:2.

3. The isolated protein of claim 2, wherein the protein inhibits the binding of TGF-β to its receptor.

4. The isolated protein of claim 3, wherein the receptor is TβRII.

5. The isolated protein of claim 2, wherein the fragment comprises at least about 100 amino acids of the C-terminal portion of SEQ ID NO:2.

6. The isolated protein of claim 2, wherein the fragment comprises at least about 75 amino acids of the C-terminal portion of SEQ ID NO:2.

7. The isolated protein of claim 2, wherein the fragment comprises at least about 55 amino acids of the C-terminal portion of SEQ ID NO:2.

8. The isolated homologue of claim 2, wherein the fragment differs from SEQ ID NO:2 by a deletion of at least about 40 amino acids from the N-terminus of SEQ ID NO:2.

9. The isolated homologue of claim 2, wherein the fragment differs from SEQ ID NO:2 by a deletion of at least about 60 amino acids from the N-terminus of the wild-type protein.

10. A therapeutic composition comprising the isolated Cystatin C homologue of claim 2, and a pharmaceutically acceptable carrier.

* * * * *

SEQUENCE LISTING

```
<160> NUMBER OF SEQ ID NOS: 10

<210> SEQ ID NO 1
<211> LENGTH: 818
<212> TYPE: DNA
<213> ORGANISM: Homo sapiens
<220> FEATURE:
<221> NAME/KEY: CDS
<222> LOCATION: (76)..(516)

<400> SEQUENCE: 1
cgcagcgggt cctctctatc tagctccagc ctctcgcctg cgccccactc cccgcgtccc      60
gcgtcctagc cgacc atg gcc ggg ccc ctg cgc gcc ccg ctg ctc ctg ctg     111
                Met Ala Gly Pro Leu Arg Ala Pro Leu Leu Leu Leu
                1               5                   10 gcc atc ctg gcc gtg gcc ctg gcc gtg agc ccc gcg gcc ggc tcc agt        159
Ala Ile Leu Ala Val Ala Leu Ala Val Ser Pro Ala Ala Gly Ser Ser
             15                  20                  25 ccc ggc aag ccg ccg cgc ctg gtg gga ggc ccc atg gac gcc agc gtg        207
Pro Gly Lys Pro Pro Arg Leu Val Gly Gly Pro Met Asp Ala Ser Val
         30                  35                  40 gag gag gag ggt gtg cgg cgt gca ctg gac ttt gcc gtc ggc gag tac        255
Glu Glu Glu Gly Val Arg Arg Ala Leu Asp Phe Ala Val Gly Glu Tyr
45                  50                  55                  60
```

| | | | | | | | | | | | | | | |
|---|---|---|---|---|---|---|---|---|---|---|---|---|---|---|
| aac | aaa | gcc | agc | aac | gac | atg | tac | cac | agc | cgc | gcg | ctg | cag | gtg | gtg | 303
| Asn | Lys | Ala | Ser | Asn | Asp | Met | Tyr | His | Ser | Arg | Ala | Leu | Gln | Val | Val |
| | | | 65 | | | | 70 | | | | | 75 | | | |
| cgc | gcc | cgc | aag | cag | atc | gta | gct | ggg | gtg | aac | tac | ttc | ttg | gac | gtg | 351
| Arg | Ala | Arg | Lys | Gln | Ile | Val | Ala | Gly | Val | Asn | Tyr | Phe | Leu | Asp | Val |
| | | 80 | | | | | 85 | | | | | 90 | | | |
| gag | ctg | ggc | cga | acc | acg | tgt | acc | aag | acc | cag | ccc | aac | ttg | gac | aac | 399
| Glu | Leu | Gly | Arg | Thr | Thr | Cys | Thr | Lys | Thr | Gln | Pro | Asn | Leu | Asp | Asn |
| | | 95 | | | | | 100 | | | | | 105 | | | |
| tgc | ccc | ttc | cat | gac | cag | cca | cat | ctg | aaa | agg | aaa | gca | ttc | tgc | tct | 447
| Cys | Pro | Phe | His | Asp | Gln | Pro | His | Leu | Lys | Arg | Lys | Ala | Phe | Cys | Ser |
| 110 | | | | | 115 | | | | | 120 | | | | | |
| ttc | cag | atc | tac | gct | gtg | cct | tgg | cag | ggc | aca | atg | acc | ttg | tcg | aaa | 495
| Phe | Gln | Ile | Tyr | Ala | Val | Pro | Trp | Gln | Gly | Thr | Met | Thr | Leu | Ser | Lys |
| 125 | | | | | 130 | | | | | 135 | | | | | 140 |
| tcc | acc | tgt | cag | gac | gcc | tag | gggtctgtac | cgggctggcc | tgtgcctatc | | | | | | | 546
| Ser | Thr | Cys | Gln | Asp | Ala | | | | | | | | | | |
| | | | | 145 | | | | | | | | | | | | acctcttatg cacacctccc accccctgta ttcccacccc tggactggtg gcccctgcct 606 tggggaaggt ctccccatgt gcctgcacca ggagacagac agagaaggca gcaggcggcc 666 tttgttgctc agcaaggggc tctgccctcc ctccttcctt cttgcttctc atagccccgg 726 tgtgcggtgc atacccccc acctcctgca ataaaatagt agcatcggca aaaaaaaaa 786 aaaaaaaaaa aaaaaaaaaa aaaaaaaaaa aa 818

<210> SEQ ID NO 2
<211> LENGTH: 146
<212> TYPE: PRT
<213> ORGANISM: Homo sapiens

<400> SEQUENCE: 2

Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Gly Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145

<210> SEQ ID NO 3
<211> LENGTH: 749
<212> TYPE: DNA
<213> ORGANISM: Mus musculus
<220> FEATURE:
<221> NAME/KEY: CDS
<222> LOCATION: (93)..(515)

<400> SEQUENCE: 3

```
ggcatttggg taaaagtcgc acggagtagc agcgtctgtt ctgcaccaac tcagagtctt      60
gttggagctt tatccctttg tcctagccaa cc atg gcc agc ccg ctg cgc tcc      113
                                    Met Ala Ser Pro Leu Arg Ser
                                    1               5 ttg ctg ttc ctg ctg gcc gtc ctg gcc gtg gcc tgg gcg gcg acc cca      161
Leu Leu Phe Leu Leu Ala Val Leu Ala Val Ala Trp Ala Ala Thr Pro
        10                  15                  20 aaa caa ggc ccg cga atg ttg gga gcc ccg gag gag gca gat gcc aat      209
Lys Gln Gly Pro Arg Met Leu Gly Ala Pro Glu Glu Ala Asp Ala Asn
 25                  30                  35 gag gaa ggc gtg cgg cga gcg ttg gac ttc gct gtg agc gag tac aac      257
Glu Glu Gly Val Arg Arg Ala Leu Asp Phe Ala Val Ser Glu Tyr Asn
 40                  45                  50                  55 aag ggc agc aac gat gcg tac cac agc cgc gcc ata cag gtg gtg aga      305
Lys Gly Ser Asn Asp Ala Tyr His Ser Arg Ala Ile Gln Val Val Arg
                 60                  65                  70 gct cgt aag cag ctc gtg gct gga gtg aac tat ttt ttg gat gtg gag      353
Ala Arg Lys Gln Leu Val Ala Gly Val Asn Tyr Phe Leu Asp Val Glu
             75                  80                  85 atg ggc cga act aca tgt acc aag tcc cag aca aat ttg act gac tgt      401
Met Gly Arg Thr Thr Cys Thr Lys Ser Gln Thr Asn Leu Thr Asp Cys
         90                  95                 100 cct ttc cat gac cag ccc cat ctg atg agg aag gca ctc tgc tcc ttc      449
Pro Phe His Asp Gln Pro His Leu Met Arg Lys Ala Leu Cys Ser Phe
     105                 110                 115 cag atc tac agc gtg ccc tgg aaa ggc aca cac tcc ctg aca aaa ttc      497
Gln Ile Tyr Ser Val Pro Trp Lys Gly Thr His Ser Leu Thr Lys Phe
 120                 125                 130                 135 agc tgc aaa aat gcc taa gggctgagtc tagaaggatc atgcagactg              545
Ser Cys Lys Asn Ala
                 140 ttccttactt gtgctccttc cctatagtgt ttcatctcgc agaagggtgc tccggctctg     605 gagggcaccg ccagtgtgtt tgcaccagga gacagtaaag gagctgctgc aggcaggttc     665 tgcacatctg aacagctgtc ccctggctcc actcttcttg cagtacctgc catgccttgc     725 tcaattaaaa aaaaaaaaaa ttcg                                            749
```

<210> SEQ ID NO 4
<211> LENGTH: 140
<212> TYPE: PRT
<213> ORGANISM: Mus musculus

<400> SEQUENCE: 4

```
Met Ala Ser Pro Leu Arg Ser Leu Leu Phe Leu Leu Ala Val Leu Ala
1               5                   10                  15

Val Ala Trp Ala Ala Thr Pro Lys Gln Gly Pro Arg Met Leu Gly Ala
            20                  25                  30

Pro Glu Glu Ala Asp Ala Asn Glu Glu Gly Val Arg Arg Ala Leu Asp
        35                  40                  45

Phe Ala Val Ser Glu Tyr Asn Lys Gly Ser Asn Asp Ala Tyr His Ser
    50                  55                  60

Arg Ala Ile Gln Val Val Arg Ala Arg Lys Gln Leu Val Ala Gly Val
65                  70                  75                  80

Asn Tyr Phe Leu Asp Val Glu Met Gly Arg Thr Thr Cys Thr Lys Ser
                85                  90                  95

Gln Thr Asn Leu Thr Asp Cys Pro Phe His Asp Gln Pro His Leu Met
```

```
                    100                 105                 110
          Arg Lys Ala Leu Cys Ser Phe Gln Ile Tyr Ser Val Pro Trp Lys Gly
              115                 120                 125

Thr His Ser Leu Thr Lys Phe Ser Cys Lys Asn Ala
              130                 135                 140

<210> SEQ ID NO 5
<211> LENGTH: 714
<212> TYPE: DNA
<213> ORGANISM: Rattus norvegicus
<220> FEATURE:
<221> NAME/KEY: CDS
<222> LOCATION: (53)..(475)

<400> SEQUENCE: 5
gggtaaaagc cgcgctgtcc tctcctctgc accgactctg tcctgcggaa cc atg gcc        58
                                                           Met Ala
                                                             1 agc ccg ctg cgc tcc ttg atg cta ctg ctg gcc gtc ctg gcc gtg gcc         106
Ser Pro Leu Arg Ser Leu Met Leu Leu Leu Ala Val Leu Ala Val Ala
        5                  10                  15 tgg gcc gga acc tcc agg cca ccc ccg cga ttg ttg gga gct ccg cag         154
Trp Ala Gly Thr Ser Arg Pro Pro Pro Arg Leu Leu Gly Ala Pro Gln
 20                  25                  30 gag gca gat gcc agc gag gag ggc gtg cag cga gcg ttg gac ttc gcc         202
Glu Ala Asp Ala Ser Glu Glu Gly Val Gln Arg Ala Leu Asp Phe Ala
 35                  40                  45                  50 gta agc gag tac aac aag ggc agc aac gat gcg tac cac agc cgc gcc         250
Val Ser Glu Tyr Asn Lys Gly Ser Asn Asp Ala Tyr His Ser Arg Ala
                 55                  60                  65 ata cag gtg gtg aga gct cgt aag cag ctt gtg gct gga ata aac tat         298
Ile Gln Val Val Arg Ala Arg Lys Gln Leu Val Ala Gly Ile Asn Tyr
         70                  75                  80 tat ttg gat gtg gag atg ggc cga act aca tgt acc aag tcc cag aca         346
Tyr Leu Asp Val Glu Met Gly Arg Thr Thr Cys Thr Lys Ser Gln Thr
     85                  90                  95 aat ttg act aac tgt cct ttc cac gac cag ccc cat ctg atg agg aag         394
Asn Leu Thr Asn Cys Pro Phe His Asp Gln Pro His Leu Met Arg Lys
100                 105                 110 gca ctc tgc tcc ttc cag atc tac agc gtg ccc tgg aaa ggc aca cac         442
Ala Leu Cys Ser Phe Gln Ile Tyr Ser Val Pro Trp Lys Gly Thr His
115                 120                 125                 130 acc ctg aca aaa tcc agc tgc aaa aat gcc taa gagctgagtc tcataggacc        495
Thr Leu Thr Lys Ser Ser Cys Lys Asn Ala
                135                 140 atgccaatgg tcccttactt gttccctac cctgtagtgt tttatccctg agaagggtgc         555
tccagctctg gagggcatct ccggggtgtt cccaccagga gacagtaaag aagctgctgc         615
aggcaggttc tgcacgtcag aacagctgtc ccctggttct cttctccttg cagtacctgt         675
cataccttgc tcttgctcaa ttaaaaaatt taaaaaatg                                714

<210> SEQ ID NO 6
<211> LENGTH: 140
<212> TYPE: PRT
<213> ORGANISM: Rattus norvegicus

<400> SEQUENCE: 6

Met Ala Ser Pro Leu Arg Ser Leu Met Leu Leu Leu Ala Val Leu Ala
 1               5                  10                  15

Val Ala Trp Ala Gly Thr Ser Arg Pro Pro Pro Arg Leu Leu Gly Ala
             20                  25                  30
```

```
Pro Gln Glu Ala Asp Ala Ser Glu Glu Gly Val Gln Arg Ala Leu Asp
         35                  40                  45

Phe Ala Val Ser Glu Tyr Asn Lys Gly Ser Asn Asp Ala Tyr His Ser
 50                  55                  60

Arg Ala Ile Gln Val Val Arg Ala Arg Lys Gln Leu Val Ala Gly Ile
 65                  70                  75                  80

Asn Tyr Tyr Leu Asp Val Glu Met Gly Arg Thr Thr Cys Thr Lys Ser
                 85                  90                  95

Gln Thr Asn Leu Thr Asn Cys Pro Phe His Asp Gln Pro His Leu Met
            100                 105                 110

Arg Lys Ala Leu Cys Ser Phe Gln Ile Tyr Ser Val Pro Trp Lys Gly
        115                 120                 125

Thr His Thr Leu Thr Lys Ser Ser Cys Lys Asn Ala
    130                 135                 140

<210> SEQ ID NO 7
<211> LENGTH: 735
<212> TYPE: DNA
<213> ORGANISM: Bos taurus
<220> FEATURE:
<221> NAME/KEY: CDS
<222> LOCATION: (56)..(502)

<400> SEQUENCE: 7
```

| | | |
|---|---|---|
| atgctagcac ccgcggatcg ccccctcgact gcagtcttttt tgcatccgag agacc atg<br>                                                                                                                                     Met<br>                                                                                                                                    1 | | 58 |

```
gtg ggc tcc ccg cgc gcc cca ctg ctc ctg ctg gca tcc ctg atc gtc      106
Val Gly Ser Pro Arg Ala Pro Leu Leu Leu Leu Ala Ser Leu Ile Val
         5                  10                  15 gcc ctg gcc ctg gcc ctg gcc gtg agc ccc gcg gca gcg cag ggc cct      154
Ala Leu Ala Leu Ala Leu Ala Val Ser Pro Ala Ala Ala Gln Gly Pro
     20                  25                  30 agg aag ggt cgc ctg ctg ggc ggc ctg atg gag gcg gac gtc aat gag      202
Arg Lys Gly Arg Leu Leu Gly Gly Leu Met Glu Ala Asp Val Asn Glu
 35                  40                  45 gag ggc gtg cag gag gcg ctg tcc ttt gcg gtc agc gag ttc aac aag      250
Glu Gly Val Gln Glu Ala Leu Ser Phe Ala Val Ser Glu Phe Asn Lys
 50                  55                  60                  65 cgg agc aac gac gct tac cag agc cgc gtg gtg cgc gtg gtg cgc gcc      298
Arg Ser Asn Asp Ala Tyr Gln Ser Arg Val Val Arg Val Val Arg Ala
                 70                  75                  80 cgc aag cag gtc gtg tca ggg atg aac tat ttc ttg gac gtg gag ctt      346
Arg Lys Gln Val Val Ser Gly Met Asn Tyr Phe Leu Asp Val Glu Leu
             85                  90                  95 ggc cgg act aca tgt acc aag tcc cag gcc aac tta gac agc tgt ccc      394
Gly Arg Thr Thr Cys Thr Lys Ser Gln Ala Asn Leu Asp Ser Cys Pro
        100                 105                 110 ttc cat aac cag ccg cac ctg aag agg gaa aag ctg tgc tcc ttc cag      442
Phe His Asn Gln Pro His Leu Lys Arg Glu Lys Leu Cys Ser Phe Gln
    115                 120                 125 gtt tac gtc gtc cca tgg atg aac acc atc aac ctg gtg aag ttt agc      490
Val Tyr Val Val Pro Trp Met Asn Thr Ile Asn Leu Val Lys Phe Ser
130                 135                 140                 145 tgc cag gat taa caggcaggcc actgaccgcc tctcactcat gctcctgcag           542
Cys Gln Asp agtgcccaca cttgtggtgg gtgactgcct actggccgtg ccttcccat gccgccctg       602 cagacacagg ctccttggc attgtctgat ctgccagggg gactctaact cgtttctttc      662
```

```
ttctaattgc tttccaagtg catggtgctc tgctattta ctcaataaaa aagtaacagc      722
agctaaaaaa aaa                                                        735
```

```
<210> SEQ ID NO 8
<211> LENGTH: 148
<212> TYPE: PRT
<213> ORGANISM: Bos taurus

<400> SEQUENCE: 8

Met Val Gly Ser Pro Arg Ala Pro Leu Leu Leu Ala Ser Leu Ile
1               5                   10                  15

Val Ala Leu Ala Leu Ala Leu Ala Val Ser Pro Ala Ala Gln Gly
                20                  25                  30

Pro Arg Lys Gly Arg Leu Leu Gly Gly Leu Met Glu Ala Asp Val Asn
        35                  40                  45

Glu Gly Val Gln Glu Ala Leu Ser Phe Ala Val Ser Glu Phe Asn
    50                  55                  60

Lys Arg Ser Asn Asp Ala Tyr Gln Ser Arg Val Arg Val Val Arg
65                  70                  75                  80

Ala Arg Lys Gln Val Val Ser Gly Met Asn Tyr Phe Leu Asp Val Glu
                85                  90                  95

Leu Gly Arg Thr Thr Cys Thr Lys Ser Gln Ala Asn Leu Asp Ser Cys
            100                 105                 110

Pro Phe His Asn Gln Pro His Leu Lys Arg Glu Lys Leu Cys Ser Phe
        115                 120                 125

Gln Val Tyr Val Val Pro Trp Met Asn Thr Ile Asn Leu Val Lys Phe
    130                 135                 140

Ser Cys Gln Asp
145
```

```
<210> SEQ ID NO 9
<211> LENGTH: 441
<212> TYPE: DNA
<213> ORGANISM: Macaca mulatta
<220> FEATURE:
<221> NAME/KEY: CDS
<222> LOCATION: (1)..(441)

<400> SEQUENCE: 9 atg gcc ggg ccc ctg cgc gcc ccg ctg ctc ctg ctg gcc atc ctg gcc      48
Met Ala Gly Pro Leu Arg Ala Pro Leu Leu Leu Ala Ile Leu Ala
1               5                   10                  15 gtg gct ctg gca gtg agc ccc gcg gcc gga gcg agt ccc ggg aag ccg      96
Val Ala Leu Ala Val Ser Pro Ala Ala Gly Ala Ser Pro Gly Lys Pro
                20                  25                  30 ccg cgc cta gtg ggc ggc ccc atg gac gcc agc gtg gag gag gag ggt     144
Pro Arg Leu Val Gly Gly Pro Met Asp Ala Ser Val Glu Glu Glu Gly
        35                  40                  45 gtg cgg cgt gcc ctg gac ttt gcc gtc agc gag tac aac aaa gcc agc     192
Val Arg Arg Ala Leu Asp Phe Ala Val Ser Glu Tyr Asn Lys Ala Ser
    50                  55                  60 aac gac atg tac cac agc cgc gcg ctg cag gtg gtg cgc gcc cgc aag     240
Asn Asp Met Tyr His Ser Arg Ala Leu Gln Val Val Arg Ala Arg Lys
65                  70                  75                  80 cag atc gta gct ggg gtg aac tac ttc ttg gac gtg gag ttg ggc cga     288
Gln Ile Val Ala Gly Val Asn Tyr Phe Leu Asp Val Glu Leu Gly Arg
                85                  90                  95 acc aca tgt acc aag acc cag ccc aac ttg gac aac tgc ccc ttc cat     336
Thr Thr Cys Thr Lys Thr Gln Pro Asn Leu Asp Asn Cys Pro Phe His
            100                 105                 110
```

-continued

```
gaa cag cca cat ctg aag agg aaa gca ttc tgc tct ttc cag atc tac    384
Glu Gln Pro His Leu Lys Arg Lys Ala Phe Cys Ser Phe Gln Ile Tyr
            115                 120                 125 act gtg cct tgg cag ggc aca atg acc ttg tcg aaa tcc acc tgt cag    432
Thr Val Pro Trp Gln Gly Thr Met Thr Leu Ser Lys Ser Thr Cys Gln
        130                 135                 140 gac gcc tag                                                        441
Asp Ala
145

<210> SEQ ID NO 10
<211> LENGTH: 146
<212> TYPE: PRT
<213> ORGANISM: Macaca mulatta

<400> SEQUENCE: 10

Met Ala Gly Pro Leu Arg Ala Pro Leu Leu Leu Ala Ile Leu Ala
1               5                   10                  15

Val Ala Leu Ala Val Ser Pro Ala Ala Gly Ala Ser Pro Gly Lys Pro
            20                  25                  30

Pro Arg Leu Val Gly Gly Pro Met Asp Ala Ser Val Glu Glu Glu Gly
        35                  40                  45

Val Arg Arg Ala Leu Asp Phe Ala Val Ser Glu Tyr Asn Lys Ala Ser
    50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
            85                  90                  95

Thr Thr Cys Thr Lys Thr Gln Pro Asn Leu Asp Asn Cys Pro Phe His
                100                 105                 110

Glu Gln Pro His Leu Lys Arg Lys Ala Phe Cys Ser Phe Gln Ile Tyr
            115                 120                 125

Thr Val Pro Trp Gln Gly Thr Met Thr Leu Ser Lys Ser Thr Cys Gln
        130                 135                 140

Asp Ala
145
```